US007501094B2

(12) United States Patent
Bysouth et al.

(10) Patent No.: US 7,501,094 B2
(45) Date of Patent: Mar. 10, 2009

(54) PREPARATION AND CHARACTERIZATION OF FORMULATIONS IN A HIGH THROUGHPUT MODE

(75) Inventors: Stephen Robert Bysouth, Columbia, MD (US); Sidney Wilson Hite, III, Elicott City, MD (US); John Henry Nettleton-Hammond, Finchampstead (GB); Karin Ingegärd Bergström, Hälta (SE); Amrish Bohara, Enschede (NL); Rowena Roshanthi Landham, Tunstall (GB); Ingrid Gunborg Lukkari, Kareby (SE)

(73) Assignee: Syngenta Limited (GB)

( * ) Notice: Subject to any disclaimer, the term of this patent is extended or adjusted under 35 U.S.C. 154(b) by 875 days.

(21) Appl. No.: 10/662,142

(22) Filed: Sep. 15, 2003

(65) Prior Publication Data

US 2005/0058574 A1 Mar. 17, 2005

(51) Int. Cl.
*B01L 3/02* (2006.01)
*G01N 21/00* (2006.01)
(52) U.S. Cl. .............................. 422/63; 422/64; 422/65; 422/66; 422/67; 422/68.1
(58) Field of Classification Search .................. 422/100, 422/63–67, 68.1
See application file for complete search history.

(56) References Cited

U.S. PATENT DOCUMENTS

| | | | | | |
|---|---|---|---|---|---|
| 4,927,545 | A | * | 5/1990 | Roginski | 210/745 |
| 5,260,872 | A | * | 11/1993 | Copeland et al. | 435/13 |
| 5,431,201 | A | * | 7/1995 | Torchia et al. | 141/98 |
| 5,587,129 | A | * | 12/1996 | Kurosaki et al. | 422/64 |
| 5,620,898 | A | * | 4/1997 | Yaremko et al. | 436/45 |
| 5,639,425 | A | * | 6/1997 | Komiyama et al. | 422/63 |
| 5,833,925 | A | * | 11/1998 | Shu et al. | 422/63 |
| 6,143,573 | A | * | 11/2000 | Rao et al. | 436/180 |
| 6,351,690 | B1 | * | 2/2002 | Lenz | 700/245 |
| 6,537,434 | B1 | * | 3/2003 | McGrath et al. | 204/459 |
| 6,565,809 | B1 | * | 5/2003 | Itoh | 422/67 |
| 6,674,022 | B2 | * | 1/2004 | Fermier et al. | 177/60 |
| 6,691,748 | B1 | * | 2/2004 | Tajima | 141/130 |

(Continued)

*Primary Examiner*—Brian R. Gordon
(74) *Attorney, Agent, or Firm*—William A. Teoli, Jr.

(57) ABSTRACT

The invention is an automated robotic system for the production and testing of formulations at a very high throughput. It is an integrated system of hardware and software capable of preparing and evaluating hundreds of emulsions per day. The system can formulate aqueous solutions (SL), oil in water emulsions (EW), suspo-emulsions (SE), micro capsule suspensions (CS), micro-emulsions (ME), and suspension concentrates (SC) at the 1 ml to 25 ml scale. The system can process emulsions rapidly in an automated way and enable very flexible formulation recipes to be introduced.

The system allows chemists to generate experimental samples of varying recipe and method to be conducted in parallel with projected throughput of up to 1200 formulations processed and characterized per day. Materials and consumables can be distributed from storage storage systems to the work stations where dispensing of ingredients in various states can be performed, including solids, liquids, gels, pastes, suspensions and waxes. The emulsions formed can be characterized using methods including phase diagnosis, turbidity analysis, viscosity and particle sizing using automated test equipment. An integrated module can also perform Tank Mix Compatibility testing in high throughput mode. The modular system allows future processes and tests to be added, either to a station, or as a new station. The software capability includes tracking of processes from start to finish and the integration of analytical data with the as-designed and as-formulated experimental results.

9 Claims, 17 Drawing Sheets

U.S. PATENT DOCUMENTS

| | | | |
|---|---|---|---|
| 6,793,887 B2 * | 9/2004 | Itoh .............................. 422/63 |
| 6,913,934 B2 * | 7/2005 | Dales et al. ................. 436/180 |
| 6,988,518 B2 * | 1/2006 | Rackers ...................... 141/130 |
| 7,169,356 B2 * | 1/2007 | Gebrian et al. ................ 422/64 |
| 7,171,863 B2 * | 2/2007 | Tamura et al. ........... 73/864.14 |
| 2003/0092185 A1 * | 5/2003 | Qureshi et al. ................ 436/43 |
| 2003/0092186 A1 * | 5/2003 | Pressman et al. .............. 436/46 |
| 2003/0194349 A1 * | 10/2003 | Carey et al. ................... 422/63 |
| 2004/0005714 A1 * | 1/2004 | Safar et al. .................... 436/43 |
| 2004/0047765 A1 * | 3/2004 | Gordon et al. ................ 422/63 |
| 2004/0241875 A1 * | 12/2004 | Dales et al. ................. 436/180 |
| 2006/0057029 A1 * | 3/2006 | Coassin et al. .............. 422/100 |
| 2006/0165562 A1 * | 7/2006 | Matsubara et al. .......... 422/100 |

* cited by examiner

PREPARATION AND CHARACTERIZATION OF FORMULATIONS IN A HIGH THROUGHPUT MODE

FIELD OF THE INVENTION

This invention relates generally to an automated robotic system for the production and testing of formulations at a very high throughput. More specifically, it is an integrated system of hardware and software capable of preparing and evaluating hundreds of dispersed multi-phase solutions per day. The system can process formulations rapidly in an automated way and enable very flexible formulation recipes to be introduced. Up to 1200 formulations on the 1 to 20 mL scale can be made per day. This includes tracking of processes from start to finish and the integration of analytical data with the as-designed and as-formulated experimental results. Materials and consumables can be distributed from storage systems to the work stations where dispensing of ingredients in various states can be performed, including solids, liquids, gels, pastes, suspensions and waxes. The emulsions, dispersions, and/or solutions formed can be characterized using methods including phase diagnosis, turbidity analysis, viscosity and particle sizing. The modular system allows future processes and tests to be added, either to a station, or as a new station.

BACKGROUND OF THE INVENTION

Formulation chemists in the Surface Actives Ingredients (surfactants) and agrochemical markets realize the potential for applying Design of Experiments (DOE) methods to assess the impact of many variables on the performance, shelf-life, delivery characteristics, contamination susceptibility, and customer satisfaction of their products. Due to the complexity of the formulation recipes and the number of variables to be evaluated, DOE techniques generate matrices of tens of thousands of experiments that must be conducted to explore and refine the experimental space for these products. The shear number of experiments required renders typical bench chemistry techniques ineffective. The invention described herein provides the formulation chemist with a means of tackling these large DOE matrices in an automated fashion.

The Summary of the Invention is followed by a Detailed Description of the system. Finally, a Process Description provides step-by-step preparation and testing methodologies for a typical Solution in Water (SL) recipe and a Suspension Concentrate (SC) formulation recipe that is prepared and tested on the invention.

SUMMARY OF THE INVENTION

The invention is an automated robotic system for the production and testing of formulations at a very high throughput. It is an integrated system of hardware and software capable of preparing and evaluating hundreds of dispersed multi-phase solutions per day. The system can formulate aqueous solutions (SL), oil in water emulsions (EW), suspo-emulsions (SE), micro capsule suspensions (CS), micro-emulsions (ME), and suspension concentrates (SC) at the 1 ml to 25 ml scale. The system can process emulsions rapidly in an automated way and enable very flexible formulation recipes to be introduced.

The system allows chemists to generate experimental samples of varying recipe and method to be conducted in parallel with projected throughput of up to 1200 formulations processed and characterized per day. Materials and consumables can be distributed from storage systems to the work stations where dispensing of ingredients in various states can be performed, including solids, liquids, gels, pastes, suspensions and waxes. The emulsions formed can be characterized using methods including phase diagnosis, turbidity analysis, viscosity and particle sizing using automated test equipment. An integrated module can also perform Tank Mix Compatibility testing in high throughput mode. The modular system allows future processes and tests to be added, either to a station, or as a new station. The software capability includes tracking of processes from start to finish and the integration of analytical data with the as-designed and as-formulated experimental results.

It is an object of the present invention to provide an automated robotic system for the production and testing of formulations.

It is a further object of the present invention to provide a system for the research, development, manufacture, and sale of products for use in agriculture, horticulture, forestry and protection during transport or storage or use of the harvested products of agriculture, horticulture or forestry and the treatment of the environment to combat infestations of pests harmful to public health, safety or convenience.

It is a further object of the present invention to provide such a system for the discovery and development of crop protection or crop enhancement products and products for the treatment of the environment to combat infestation of pests harmful to public health, safety or convenience.

It is a further object of the present invention to provide such a system for the research, development, manufacture and/or sale of surfactants, fatty acids and rheology control agents in formulations for fabric care, personal care, textile, mining, mineral coating, asphalt, petroleum, fuels, viscose, cleaning, building, coatings, paper processing and manufacture and in all applications of nitrogen derived surfactants.

DETAILED DESCRIPTION OF THE INVENTION

An automated robotic system is disclosed herein for the production and testing of formulations at a very high throughput. In a preferred embodiment, a run is considered to be the operation of the system over a 24 hour period, including an approximately 20 hour operation period and an approximately four hour set-up period. Further, the disclosed, preferred embodiment is based upon the use of a 25 mL vial to hold about 10 mL of test formulation. The embodiment disclosed herein is disclosed for illustrative purposes only, alternative embodiments are envisioned.

Figure 1:
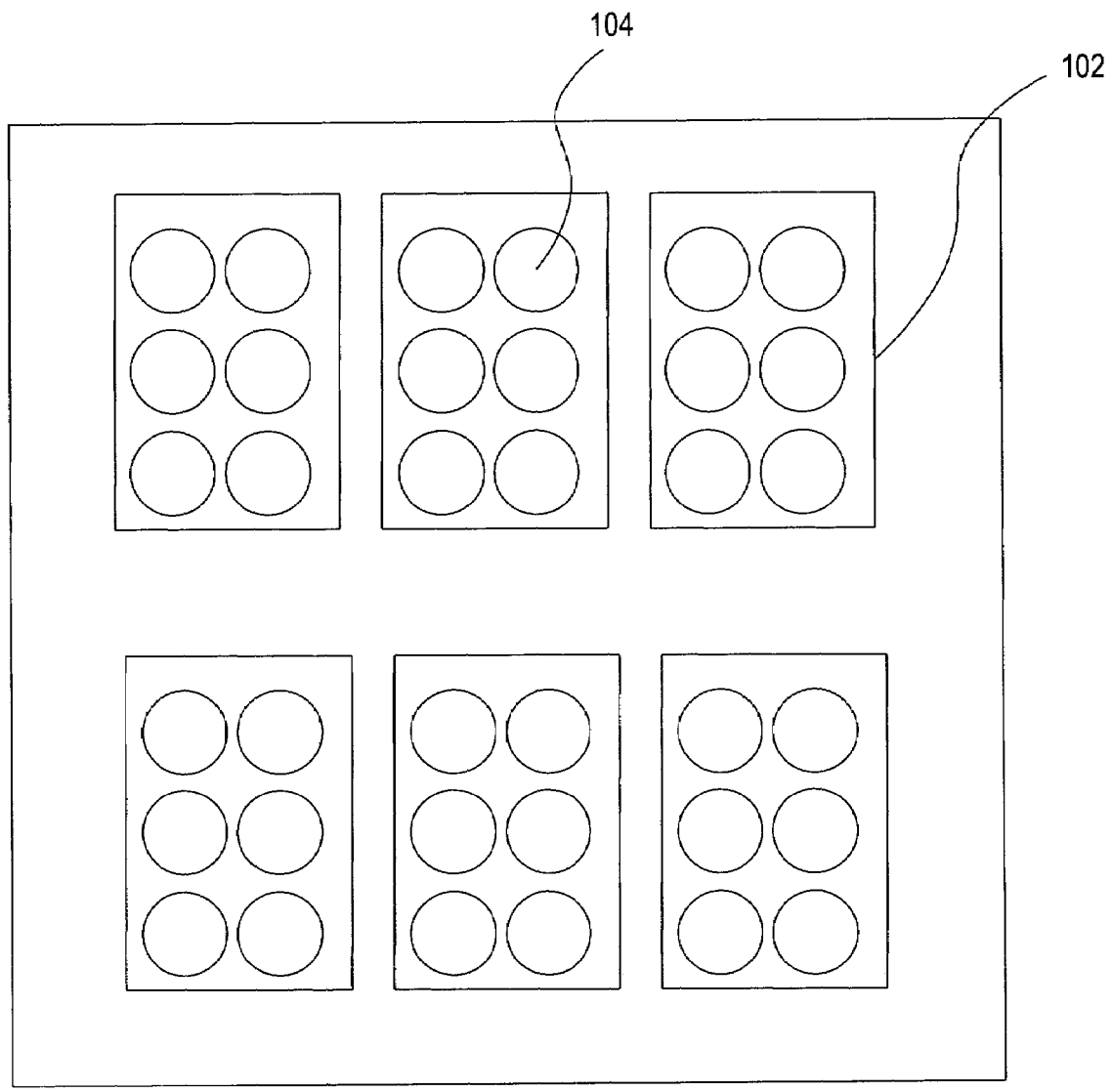
FIG. 1 illustrates rack and vial storage system 100.

FIG. 1 illustrates rack and vial storage system 100, comprising rack 102 and vial 104. Vials are of the order of 25 mL, and 24 mm diameter, 73 mm high. They are racked in racks with a 'well-plate' foot-print containing 6 vials per rack. Each vial is bar coded and each rack is bar-coded. As these are custom racks, there is likely no cost differential between having plastic racks molded or machined from metal. In fact, metal racks can provide a simpler and faster means to heat the vials, because placing a rack of vials on a hot-plate is faster than transferring vials from a rack to a heating block. In this instance too, less space is needed on a robot deck, as empty racks are not generated, diminishing the need for storage.

Figure 2:
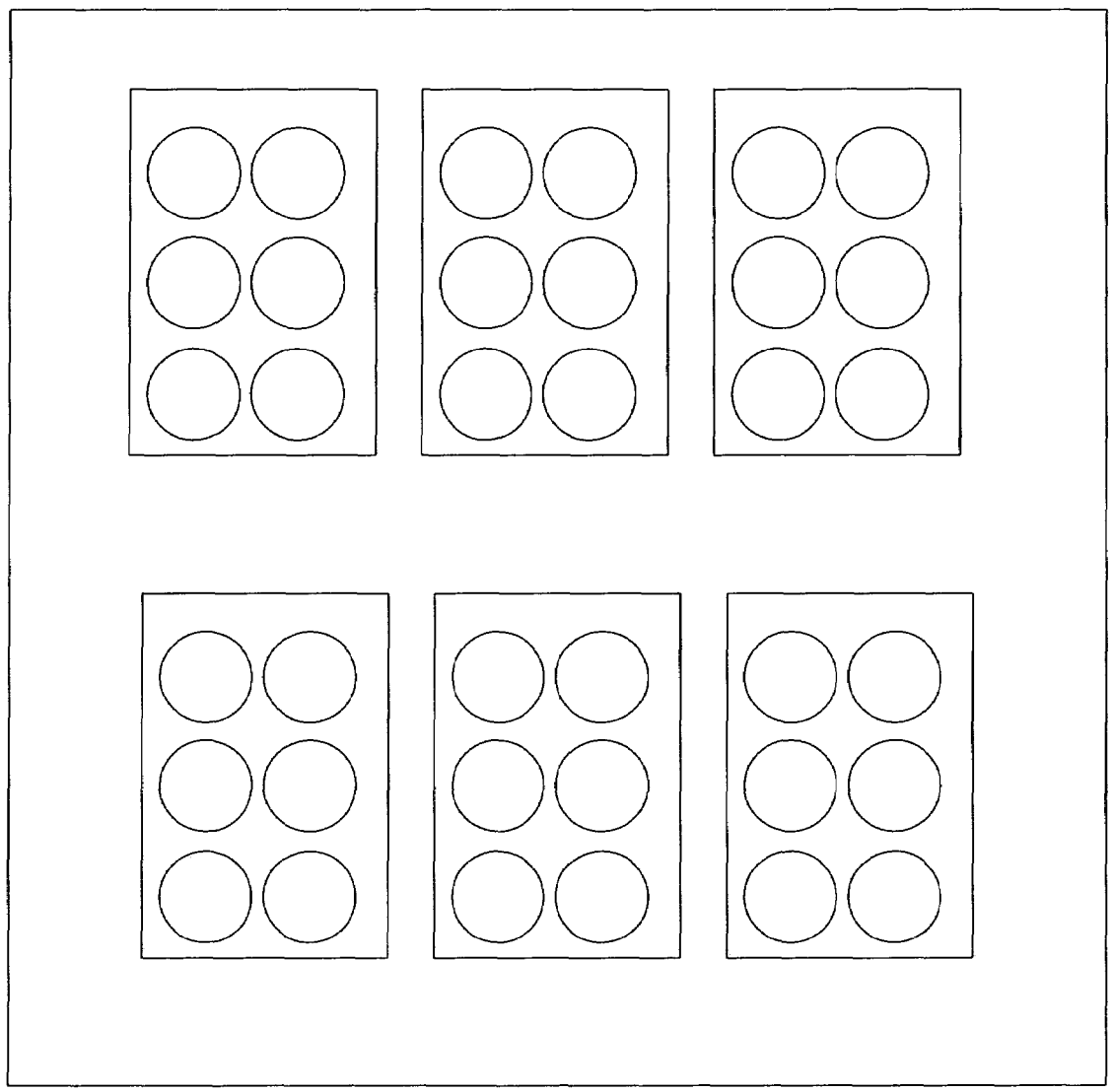
FIG. 2 illustrates consumables store 200.

FIG. 2 illustrates consumables station 200. These are used to supply the materials needed for a run including vials, pipette tips and, optionally, materials to be dispensed. The number and size of the storage systems will depend on the manufacturer, vial size and functions as above, selected by the customer.

There are many manufacturers of these storage systems or stations (for example, Zymark, CRS, TomTek, STRobotics, etc.,) and custom versions can be obtained. Standard models work with the ubiquitous 'Well-Plates' and it is intended that the system disclosed herein will rack materials in the same format, be it vials, pipette tips or even solids for dispensing. These racks can also be referred to as 'plates' but their height will not be a standard well plate height.

These stations are designed to store and present to an arm or gantry robot, individual plates in a defined position. At the beginning of a run they are loaded appropriately and at the end of a run, they contain finished formulations, grouped as needed (pass, fail, etc.,), along with empty racks and used source vessels, ready for unloading.

Capacity requirements are dependent upon the desired application. For example in one embodiment 2000 positions are provided to hold 1500 vials (leaving 500 empty) and in a second embodiment 1000 positions are provided with 600 vials (leaving 400 empty). Additionally, space is provided for consumables (for example 5000 pipette tips) and for compound supply.

Figure 3:
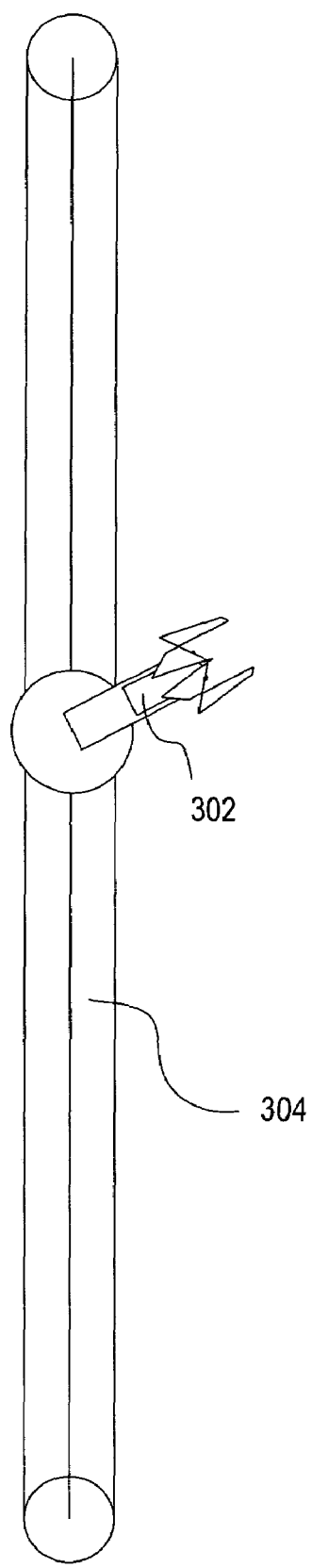
FIG. 3 illustrates robotic arm 300.

FIG. 3 illustrates robotic arm 300 showing arm 302 and rail 304. There are many robotic arm manufacturers and the most suitable arm and manufacturer are selected during the design phase for each application. The robotic arm provides the transport connection between all the stations for making and characterizing the emulsions, by moving the racked vials between the stations as required. In some embodiments the system is augmented by a second arm. Where the system is not augmented by a second arm, the sole arm also has the task of loading individual vials into the mixing systems; this requires either a gripper tool change, or the design of a dual function gripper for both vial and rack handling.

Operation of the robotic arm can be considered to be divided into three parts: set-up, where materials and racks are dispersed about the system; run, where samples and supplies are transported during making of emulsions and; clean-up, where at the end of a run, dispersed material and samples are restored to their proper location. The use of such an arm enables 'random access' type of ordering of processes supplied by the stations around the rail. In a preferred embodiment, the robotic arm has the ability to read rack identity by bar codes.

Figure 4:
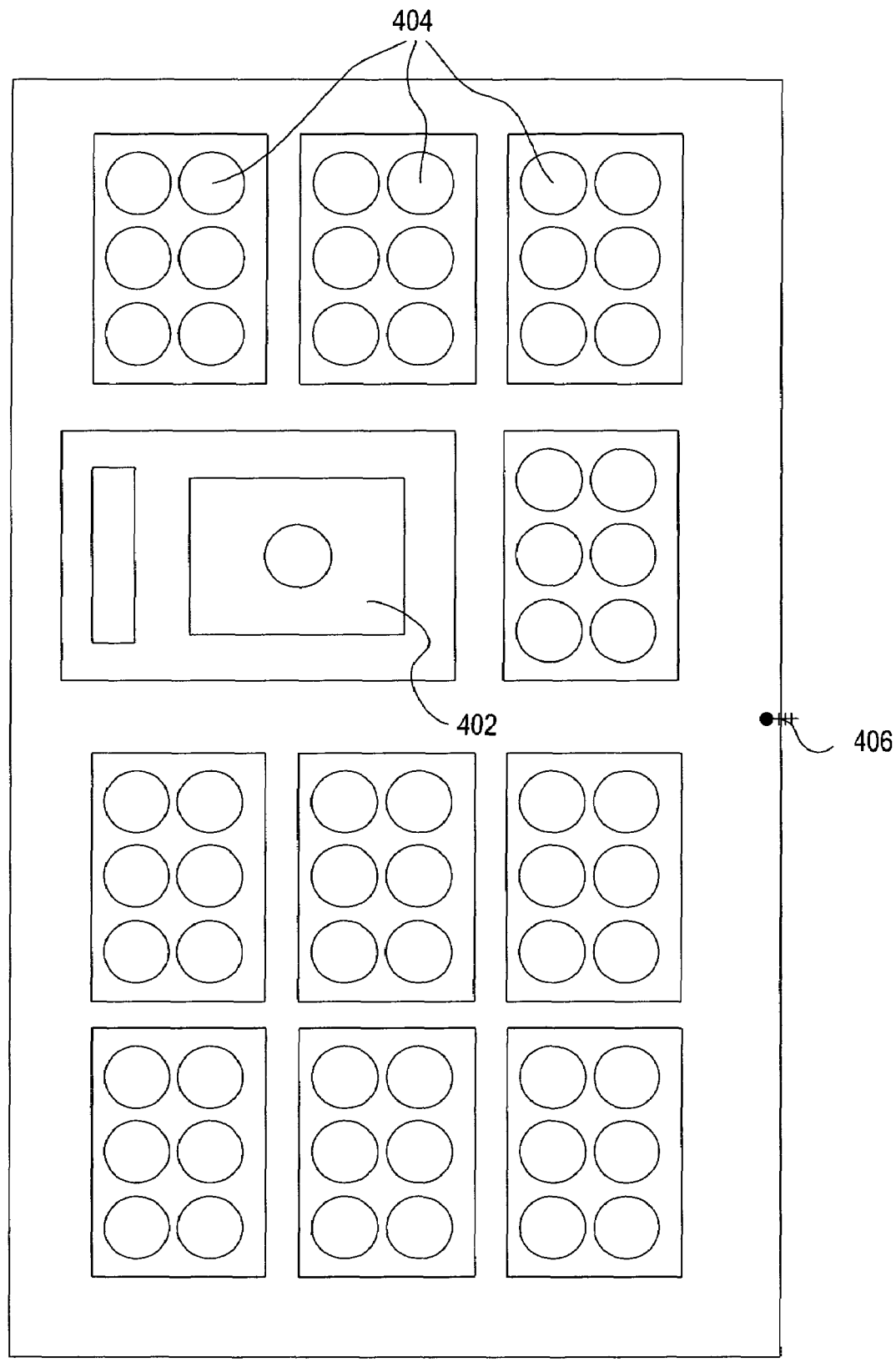
FIG. 4 illustrates solid dispensing station 400.

FIG. 4 illustrates solid dispensing station 400. Such a station can be obtained from multiple manufacturers, including Chemspeed, Autodose and Flexiweigh. The platform is adapted to suit individual requirements. The dispense accuracy of each system is dependant on the material to be dispensed. Additionally, a representative sample must be dispensed from the container in terms of particle size and chemical composition. If required, sample conditioning such as grinding and sieving can be used to prepare the powders. Dispenses of 1 mg can easily be achieved and pre-treatment of the powders will increase both accuracy and precision.

The deck is mounted with devices, the number and position of which are dependent upon the application. The devices include but are not limited to the following: bar code reader/capper/decapper 602; caps source; second pipette-tip rack space 604 liquid vial deck space; second orbital shaker 606; tank mix testing unit 608; particle-sized injection port 610; dilution port 611; viscometry injection port(s) 612; filtration device; filter elements source 614; particle size detector 618; viscometry detecor(s) 620; cap supply 622; waste station 628; bead collection 630; trash 632; photography system 624, and particle microscopy system 638.

Figure 5:
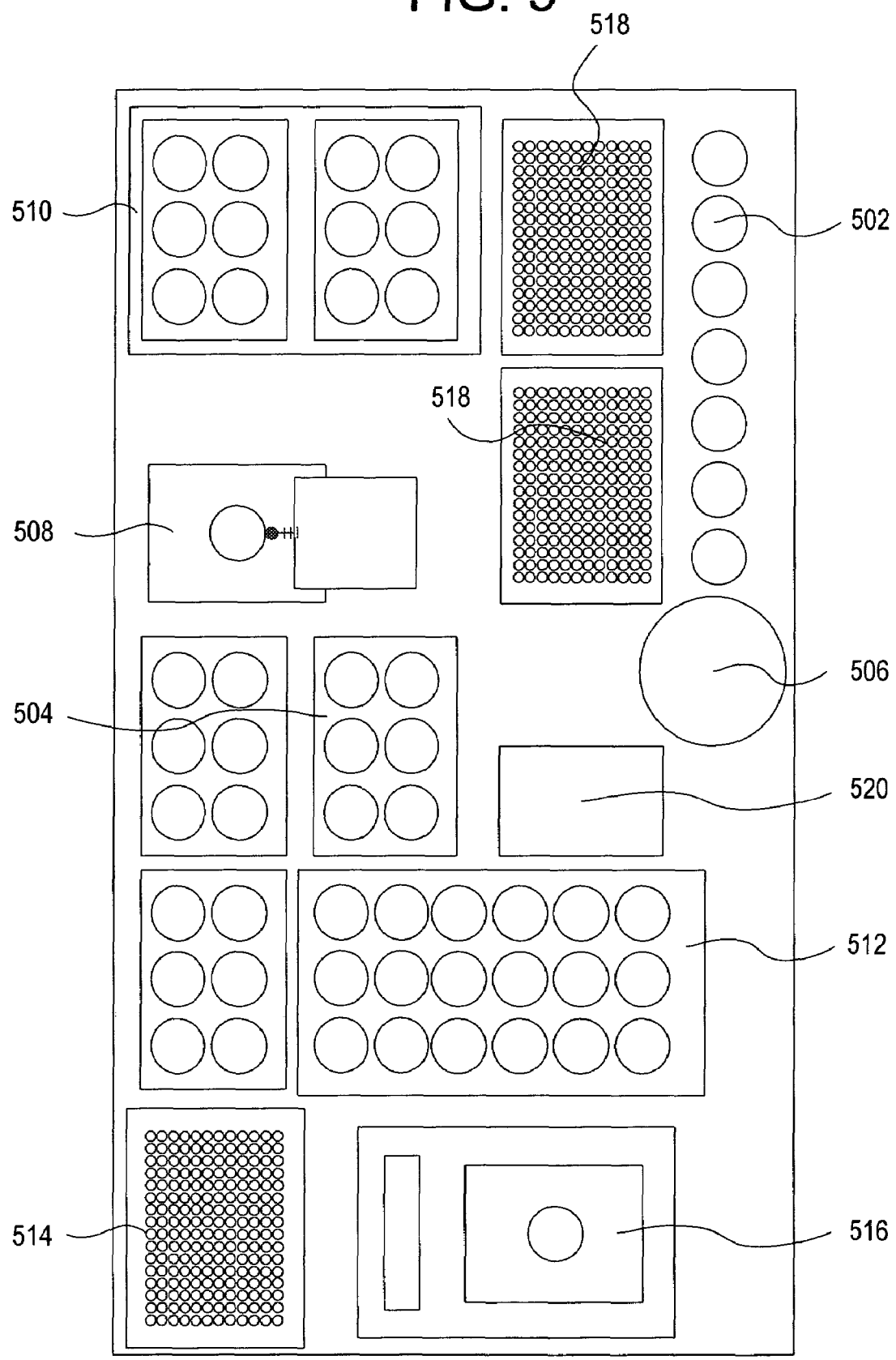
FIG. 5 illustrates an embodiment of liquids, suspensions, gels and meltables dispense station 500.

FIG. 5 illustrates an embodiment of liquids, suspensions, gels and meltables dispense station 500. This station is based upon a gantry or Cartesian laboratory robot. Again, there are many manufacturers of such systems for example the Gilson "Cyberlab" 230/240/400 type platforms. These robot systems allow up to six tools to be mounted on the tool head above the deck, and the deck can be fitted with custom equipment including sub-stations with other integral tools. In a preferred embodiment the tool head is fitted with devices such as, but not limited to: rack/plate gripper, vial and cap gripper, gel dispenser gripper if required, pipettor for small plastic disposable pipette tips, optional pipettor for glass disposable pipette tips, and vacuum canula for dispensing grinding beads.

Some tools can require more than one tool position. Some of these devices are multifunctional. For example, the vial gripper can also function as the gel dispenser gripper. Additionally, in varying embodiments, more than one size of pipette can be required for precision and accuracy in dispensing. It is envisioned that both 5 mL and 500 µL tips are used.

The deck is mounted with associated devices such as, but not limited to: movable gel dispensers 502; rack or dispensing locations 504; comminuting bead source 506, pre-loaded with beads; bar code reader/decapper 508; orbital shaker 510; one or more heated blocks 512; heated glass pipette tips 514; second mass balance 516; pipette-tip rack space 518; liquid vial deck space to enable other sources of normal liquids to be placed on the deck; enough space to contain the racks (likely stacked) that have been emptied into other deck units; and trash collection chute 520 for pipette tips and vial caps. Bar code reader/decapper 508 is used for identifying and opening vessels that arrive capped. Mixtures requiring agitation, such as unstable suspensions, are delivered to orbital shaker 510 after decapping. Orbital shaker 510 is also used for mild mixing such as dissolution and with careful selection of the shaker, even more aggressive agitation can be achieved. Where needed, materials are placed to melt upon/within the one or more heated blocks 512, the materials are then readied for dispensing. Heated glass pipette tips 514 can be preloaded to be heated for dispensing small quantities of meltables. Second mass balance 516 is used for confirming the dispense by weighing.

Because of the distribution of the tools on the head of such robots (where fixed tools are in fixed positions on the head), not all the deck space is accessible by all tools. Specifically, for example, in certain instances the right hand tool cannot reach the left hand side of the deck and visa versa. This limits the position and access for each tool to the bed. Alternatively, the gel, paste and high viscosity fluid dispensing or the meltables dispensing can require a separate station or sub station, especially when combined with mixing or when the quantities that should be dispensed, exceed 2 mL. When mixing is not required, the dispense volume can be confirmed using a balance. However, since order of addition and mixing do not allow the tip of any dispenser to contact the mixed formulation, the dispensing must be conducted without touch-off.

When a mixer is used with dispensing, the station includes a dedicated wash station in which the mixers are cleaned, along with a wash fluid reservoir, pumps, drainage and valves as required (specified during the design phase) mL and 500 µL tips are used.

Figure 6:
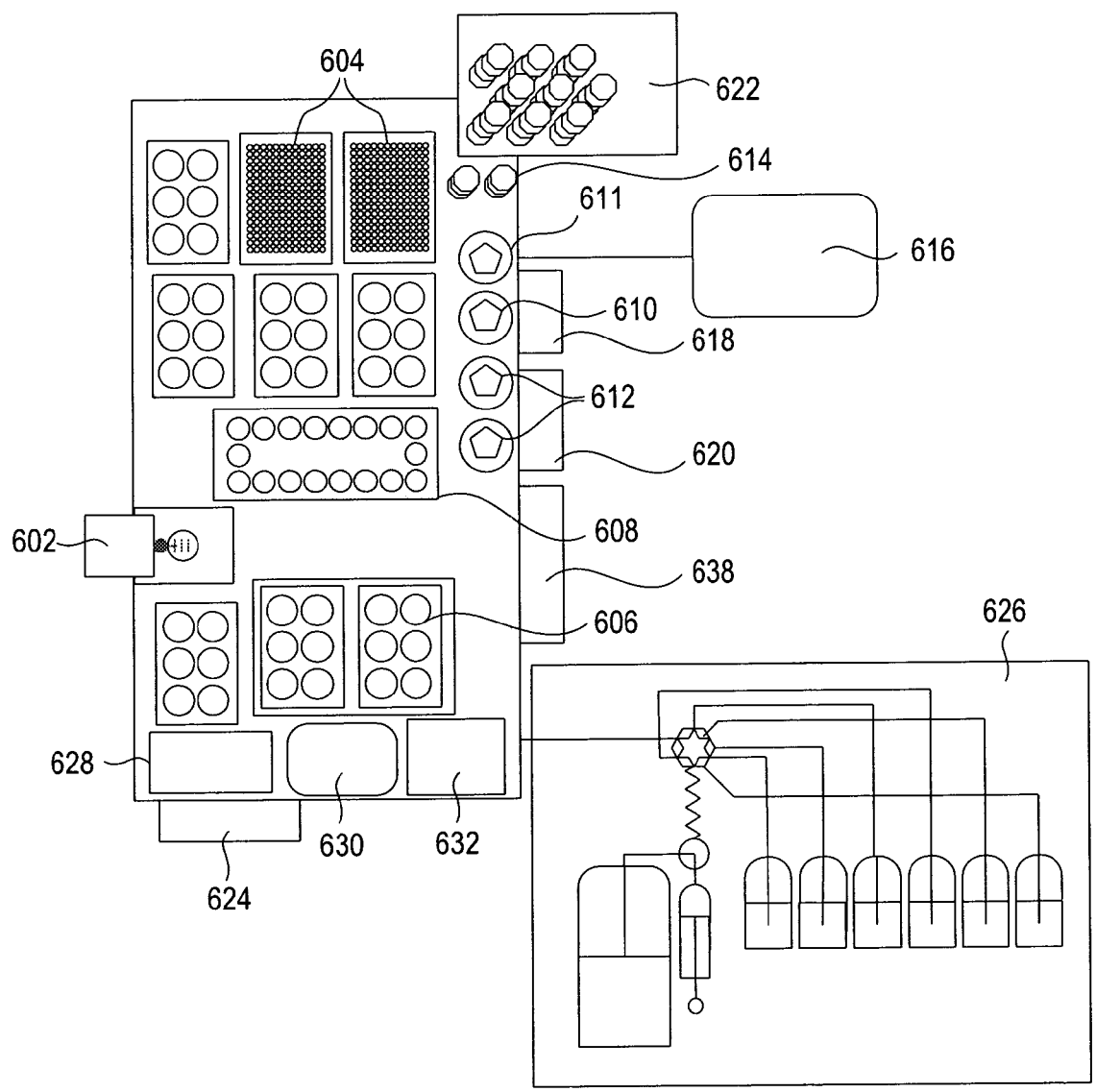
FIG. 6 illustrates normal liquids dispensing and pipetting, and characterization station 600.

FIG. 6 illustrates normal liquids dispensing and pipetting, and characterization station 600, which can be included in alternative embodiments. This station provides a pair of waste stations where two separated types of fluid can be pumped to waste, and can be preferred when fluids are incompatible. The tool head can be fitted with items such as: rack/plate gripper; vial, filter and cap gripper; pipettor for plastic disposable pipette tips; dispense needle attached to the off-deck dispensing pumps, valves and manifold; and dispense needle for dispensing a common wash fluid.

Again, some tools can require more than one tool position and in a preferred embodiment, some devices are multifunctional. As before, more than one size of pipette is required for precision and accuracy in dispensing. It is envisioned that both 5 mL and 500 µL tips would be used. Additionally, a pipettor suitable for more viscous samples can require a separate tool or replace those in the 5 mL tip rack.

The deck is mounted with devices, the number and position of which are dependent upon the application. The devices include but are not limited to the following: bar code reader/ capper/decapper 602; caps source; second pipette-tip rack space 604; liquid vial deck space; second orbital shaker 606; tank mix testing unit 608; particle-sized injection port 610; dilution port 611; viscometry injection port(s) 612; filtration device; filter elements source 614; particle size detector 618; viscometry detector(s) 620; cap supply 622; wash station 628; bead collection 630; trash 632; photography system 624, and particle microscopy system 638.

The bar code reader/capper/decapper 602 is used for identifying and opening vessels that arrive capped and for closing vials before they are sent to storage. In a preferred embodiment, a source for about 2000 caps is provided. In a preferred embodiment, pipette-tip rack space 604 comprises a source of special slotted tips for aspirating the comminuted mixture from the beads.

Liquid vial deck space enables other sources of normal liquids to be placed on the deck. Similarly, in a preferred embodiment, enough space is provided to contain the racks and to provide space for sorting sample vials into classes (e.g. once pass/fail criteria are applied). Orbital shaker 606 provides general mild to moderate mixing but is also used for Tank Mix Testing 608. Samples are pipetted into the particle-size injection port 610, the actual particle size detector 618 being mounted off deck. Dilution port 611 allows dilution of the formulation for particle photography. Viscometry injection port(s) 612 allow for measurement of viscosity at different shear rates. Filtration devices allow for timing the filtration of tank mix test samples. Filter elements obtained from filter elements source 614 are used for the tank mix test. Photography system 624 is used for photographing the tank mix test filter surface.

Off the robot deck are mounted large components of processing or measuring devices, including but not limited to: particle size detector 618, photography system 624, viscometer measurement electronics 620, valve and pump system 626 for dispensing small (10's of micro liters) volumes of samples with a 'majority solvent' flush to the dispense needle, and pump and source of common wash fluid 616 connected to its needle.

Figure 7:
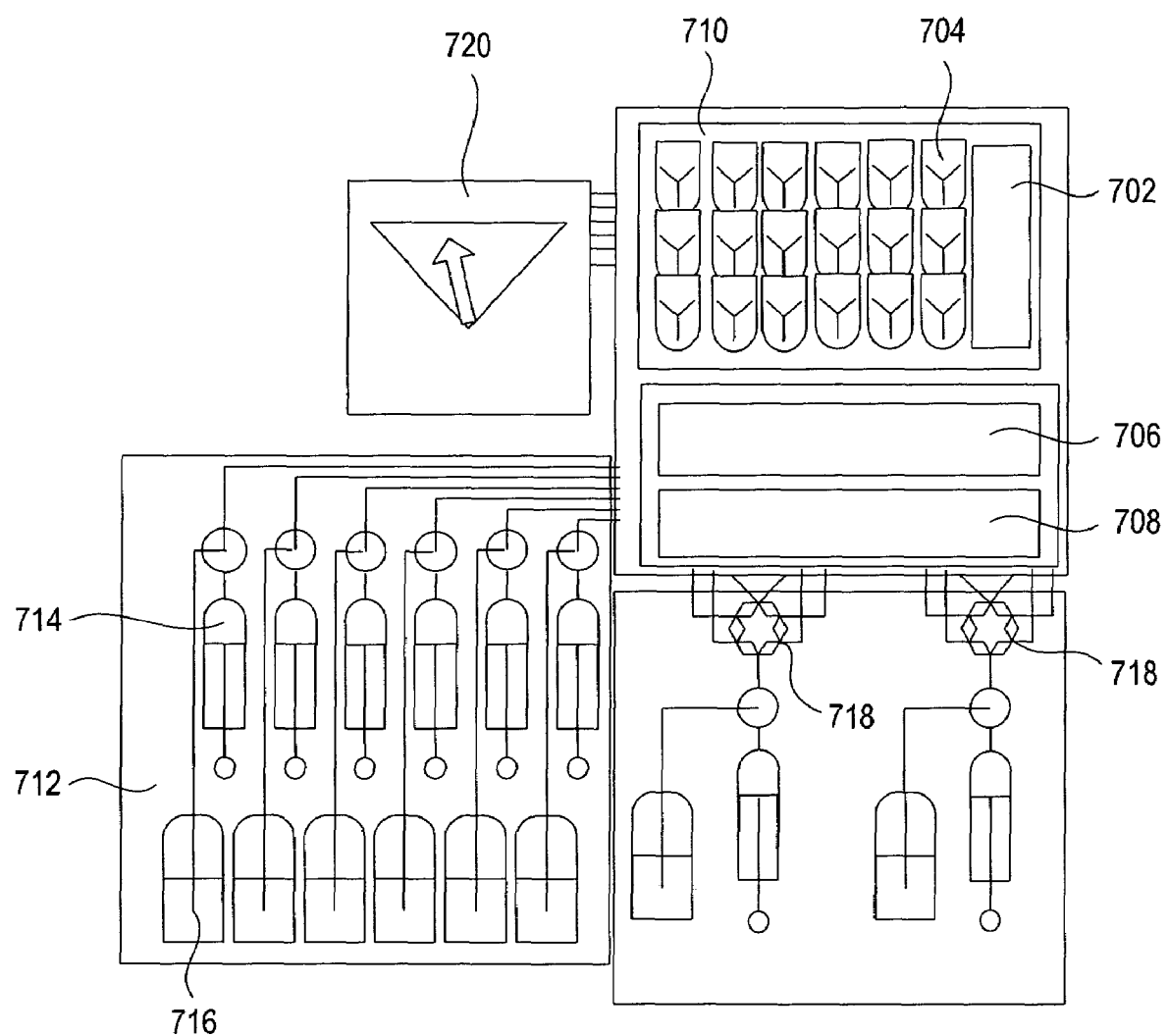
FIG. 7 illustrates mixing or homogenizing station 700.

FIG. 7 illustrates mixer/homogenizer station 700 with liquid addition. These station(s) have the ability to mix in both high and low shear mode in parallel. Stations 702 include a two axis (one vertical and one horizontal axes) Cartesian robotic system that can move up to six mixer/homogenizers 704 mounted in-line on an arm, between several rows of up to six (n×6) vessels and to an ultrasonic wash station 706 and a rinse station 708. Additionally, the vessels in which mixing is occurring can be heated or cooled via a temperature-controlled fluid jacket and a chiller/heater/circulator 710. The mixers include hardware to mount 3 probes of ⅛" diameter with their working ends at the mixer blade. These probes can be for measuring pH or tubes for dispensing fluids into the mixture connected to a liquid addition unit 712 as determined by application requirements.

The mixer/homogenizer 704 preferred capabilities include: the ability to mix in high and low shear modes; the ability to determine some measure of torque such as current vs. speed to allow a crude measure of viscosity; and a head diameter of no more than 15 mm.

The liquid addition units 712 allow specific liquid(s) to be dispensed while mixing. The liquid addition units are built from common components available from companies such as Hamilton, Cavro, Rheodyne and Valco. The numbers of designs of such devices are infinite, and those described here should be thought of as proposals to meet defined needs with the understanding that other component combinations can provide the appropriate functionality.

In a first embodiment of a liquid addition unit, each of the mixer heads is provided with one supply tube, each supplied from a separate pump 714 and source bottle 716. This allows the addition of up to six different liquids chosen by the mixer row position where the target vial is loaded. These pumps are able to quantitatively dispense moderate and low viscosity materials (flow at room temperature).

In a second embodiment of a liquid addition unit, the mixer system is provided with two tubes along with a combination pH electrode. In a preferred embodiment an electrode of ⅛' diameter which includes the temperature probe, is used. Fluid is supplied to each mixer/homogenizer head, one at a time, from valves 718. As described, it can be used for pH adjustment; however, it can also be used for dispensing other normal liquids if pH adjustment is not needed.

Additionally, off deck can be a pH multimeter 720 such as that available from NICO2000. Versions are available that accept up to 24 pH probes and 24 temperature probes.

Figure 8:
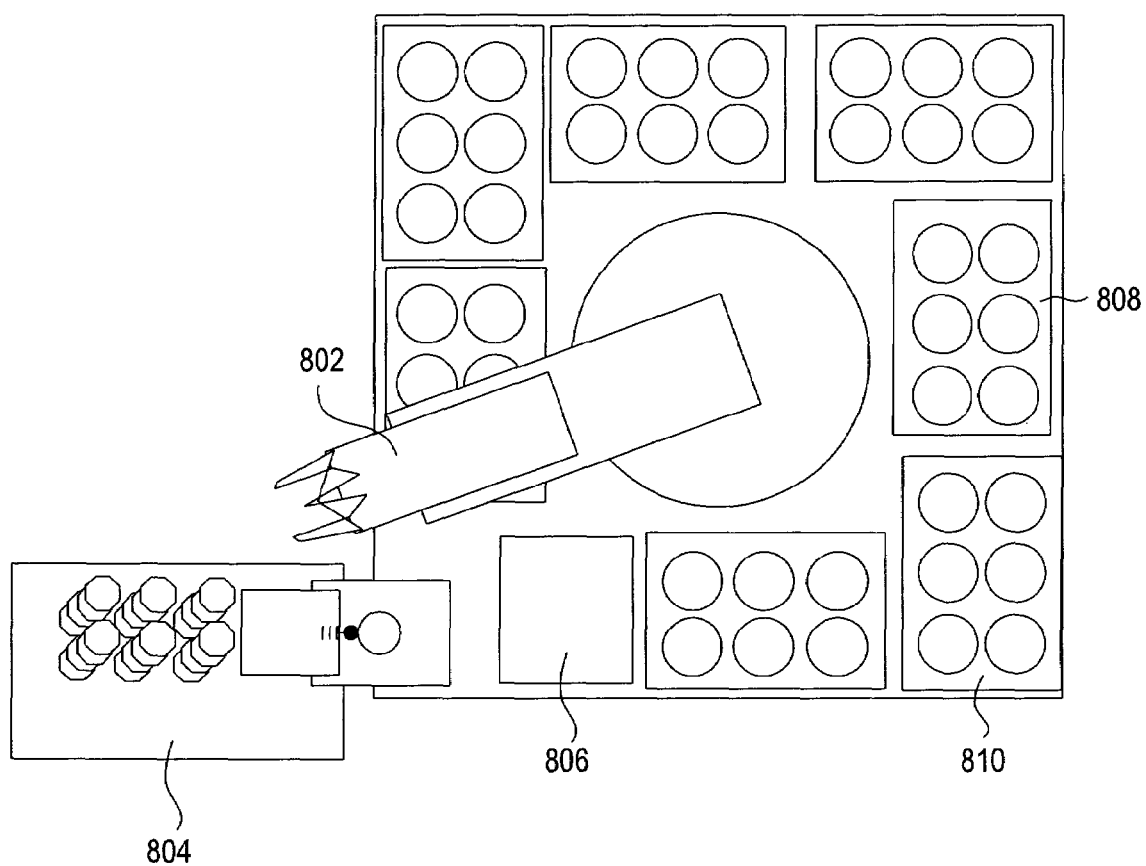
FIG. 8 illustrates flexible arm station 800 used in alternative embodiment.

FIG. 8 illustrates flexible arm station 800 used in an alternative embodiment. Flexible arm 802 accepts racks of vials from the robot arm 302 delivery point and provides individual vials to capping/decapping/bar code reading/cap supply station 804. For mixing, if caps are present, they are removed and discarded in trash bin 806 and the vials placed in the appropriate mixer location 704. Alternatively, caps can be put on the vial before it is placed in comminutor 902 by flexible arm 802. After processing, flexible arm 802 moves the vials to the capping/decapping/bar code reading/cap supply station 804 as needed and returns them to the appropriate racks.

Systems within reach of flexible arm 802 can include but are not limited to: transfer area for delivery and receipt of racks of vials 808; rack storage space for emptied racks 810; capping/decapping/bar code reading/cap supply station 804 (vials only—not racks); if flexible arm 802 is used during the de-capping, trash chute 806; off mixer station(s); and comminutor loading receptacle 904. The reach of the robot chosen is dependent upon the dimensions of the system, specifically the rack storage space and the comminutor.

Figure 9:
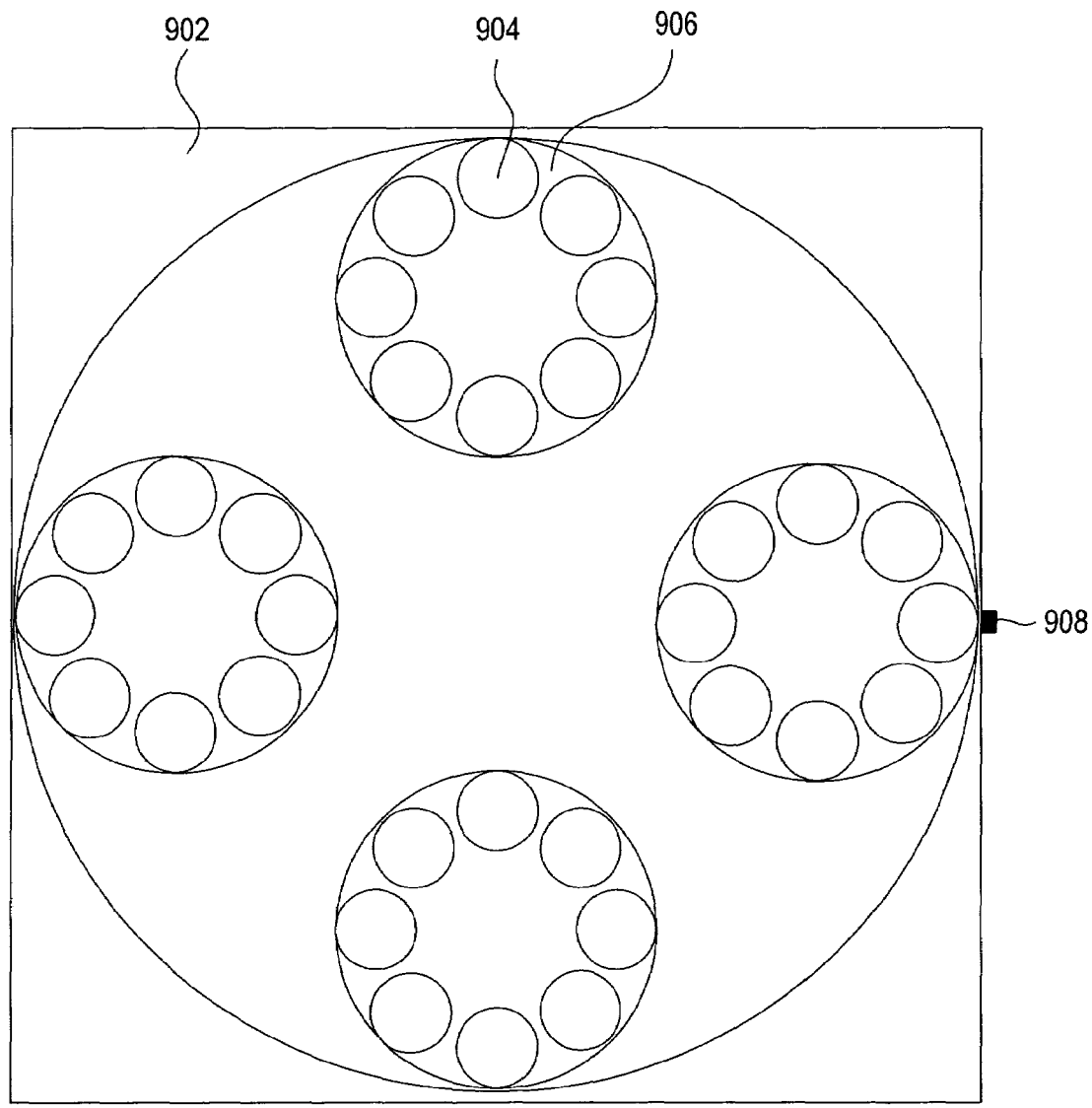
FIG. 9 illustrates comminutor station used in an alternative embodiment 900.

FIG. 9 illustrates comminution station 900 used in an alternative embodiment. In this embodiment, planetary ball mill 902 is modified and small vials of about 25 mL are placed around the periphery of vial holders 906 to provide the comminution action required for up to 32 vials in parallel. Capped vials are delivered to the mill containing solids liquids and beads. The planetary action causes the beads to roll and 'fly' in the vial, causing grinding of the solid particles. After a prescribed time, the mill returns to defined stop position 908 and the vials are extracted and racked by arm 802. Before racking, the vials can be de-capped. Whether to de-cap depends on the future of the vial. Further, vials can be stored in the space provided and de-capping delayed to allow material to settle off the lid.

Figure 10:
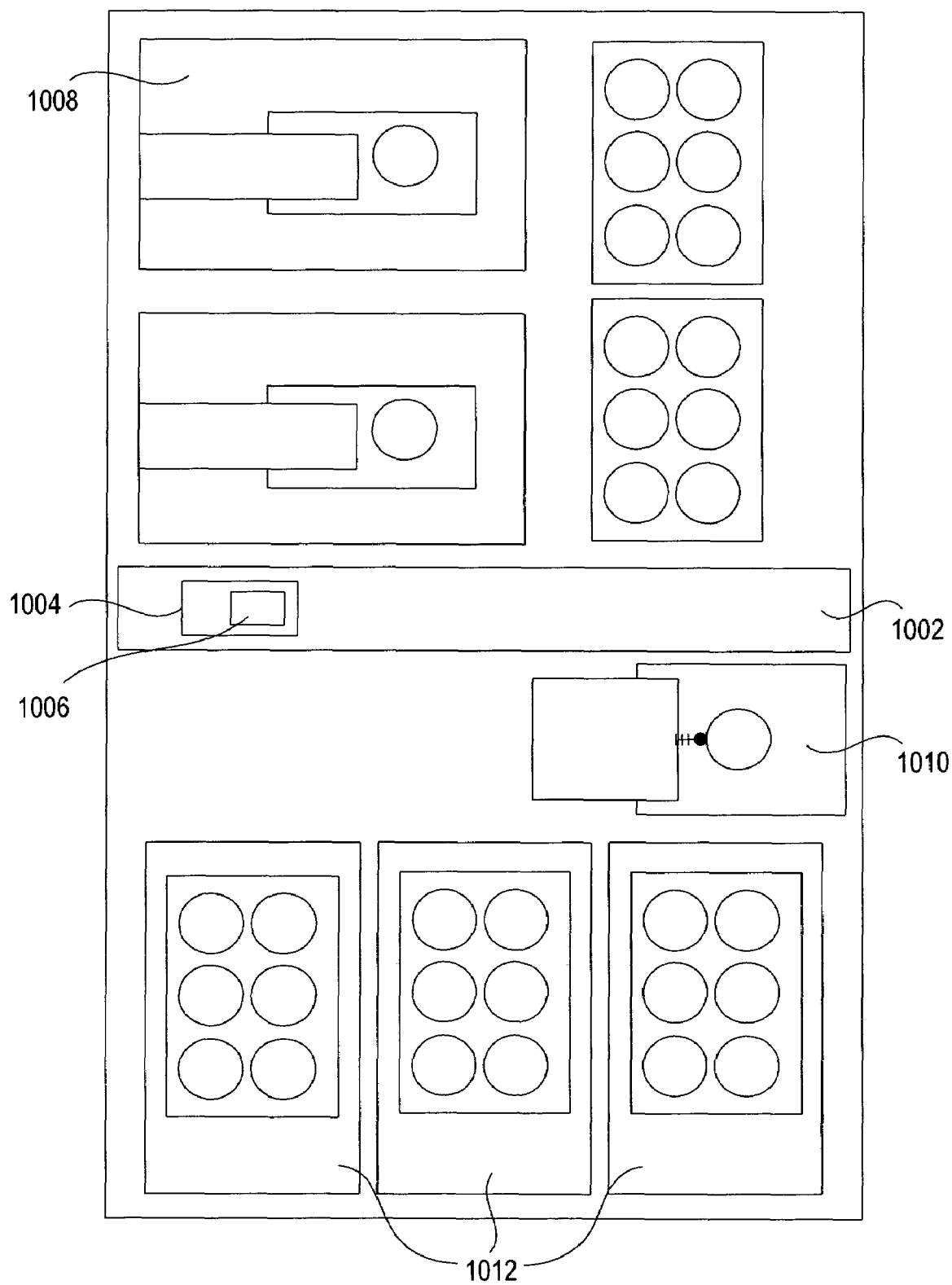
FIG. 10 illustrates phase stability and cloud point station 1000.

FIG. 10 illustrates phase stability and cloud point station 1000. Apart from torque feed-back from the mixing stations, phase stability and cloud point station 1000 is the first station visited by most samples where characterization takes place. It is based on Cartesian robotic system 1002 such as provided by Gilson. In a preferred embodiment, the only tool on the head 1004 is gripper 1006. This gripper has the ability to invert the vials if needed. Mounted on the deck are turbidity analysis instrument(s) 1008 such as Turbiscan (from Formulaction) or similar systems, bar code reader 1010, heated/cooled zones 1012 and space for at least 3 racks. Samples are delivered in racks by arm 302, and vials withdrawn and either placed in the heated/cooled zones and subsequently into the turbidity analysis instrument systems, or immediately into the turbidity analysis instrument systems where they are characterized for such properties as turbidity, phase separated, homogeneous, sedimentation, creaming, foaming etc. The ability to invert the vial just before measurement, also allows foaming and sedimentation to be studied. The vials are then removed and either placed back into the original rack, or sorted into 'pass' and 'fail' racks as determined by the selection criteria. Arm 302 then removes the racks of vials.

Figure 11:
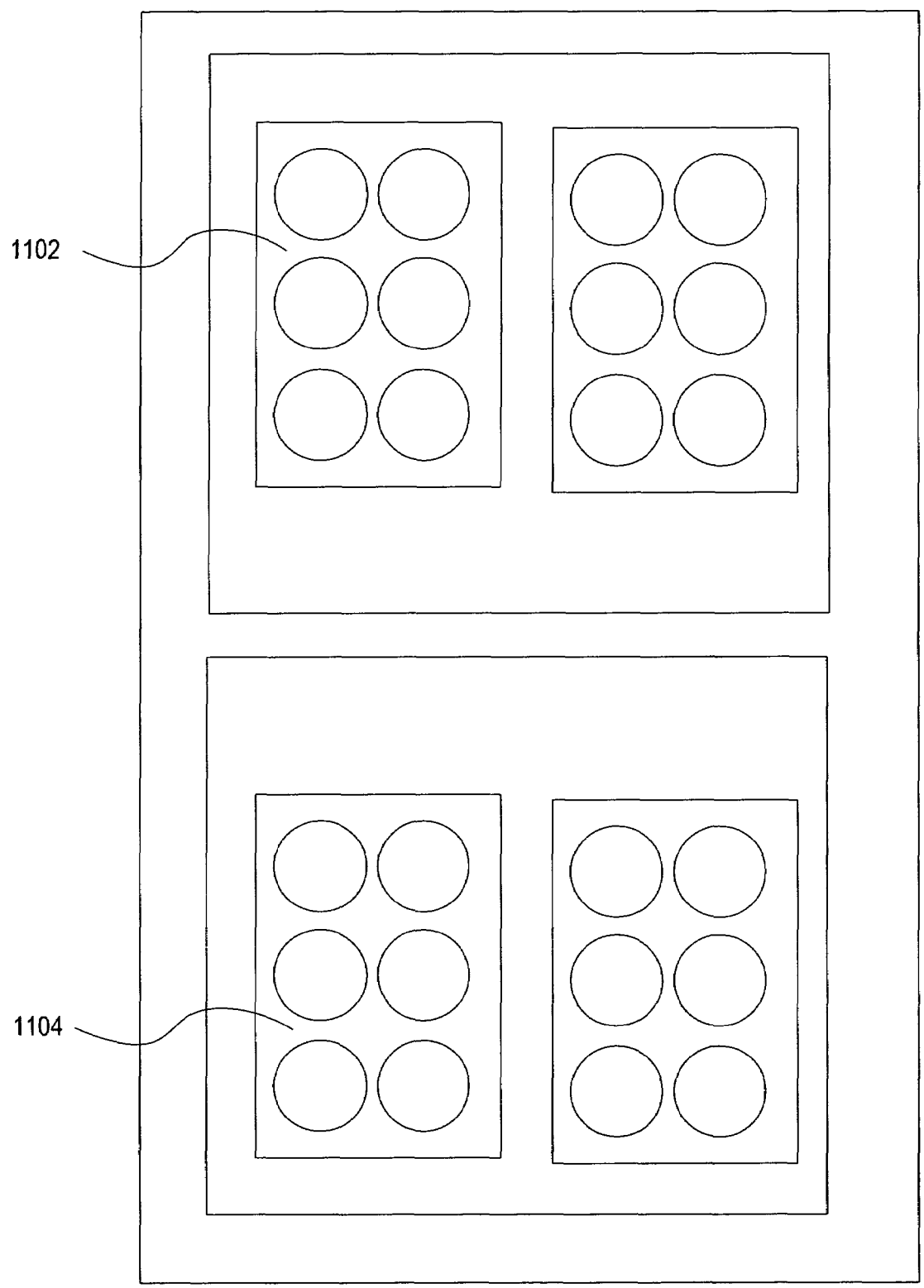
FIG. 11 illustrates buffers 1100.

FIG. 11 illustrates temperature buffers 1100. Typically, such complex automated systems need space to buffer the stations to allow processes occurring at different times and speeds, to be synchronized. Each of solid dispensing station 400; liquids, suspensions, gels and meltables station 500; normal liquids dispensing and pipetting and characterization station 600; flexible arm station 800, phase stability and cloud point station 10000; and alternate dispensing, pipetting, and characterization station 1200 naturally provides some buffer capacity and space in storage systems 100 that can also be available during an experimental campaign. However, additional space can be required. For example, two embodiments could include ambient and temperature controlled buffers 1102 and 1104, respectively. Additionally, arm 302 is then the only service that the buffers would require as these buffers would be 'dumb'.

Figure 12:
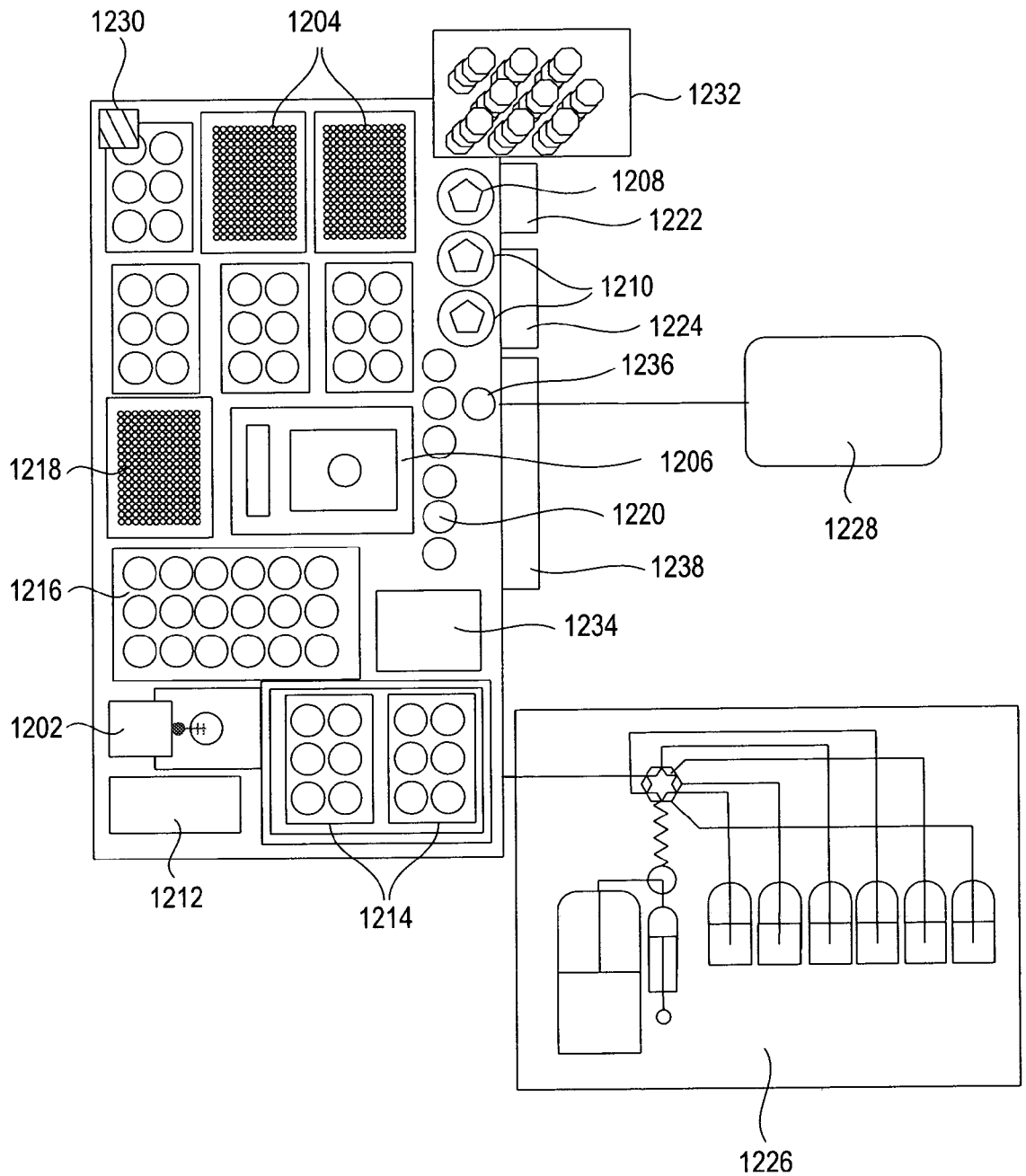
FIG. 12 illustrates dispensing, pipetting, and characterization station 1200, included in alternative embodiments.

FIG. 12 illustrates alternate dispensing, pipetting, and characterization station 1200, which can be included in alternative embodiments. This station is based upon a gantry or Cartesian Laboratory Robot. Again, there are many manufacturers of such systems such as the Gilson "Cyberlab" 230/240/400 type platforms. These robot systems allow up to six tools to be mounted on the tool head above the deck, and the deck can be fitted with custom equipment including substations with other integral tools.

The tool head can be fitted with items such as: rack/plate gripper; vial and cap gripper; gel dispenser gripper; pipettor for plastic disposable pipette tips; pipettor for glass disposable pipette tips; dispense needle attached to the off-deck dispensing pumps, valves and manifold; and dispense needle for dispensing a common wash fluid Again, some tools can require more than one tool position and in a preferred embodiment, some devices are multifunctional. As before, more than one size of pipette can be required for precision and accuracy in dispensing. It is envisioned that both 5 mL and 500 µL tips would be used. Additionally, a pipettor suitable for more viscous samples can require a separate tool or replace those in the 5 mL tip rack.

The deck can be mounted with the following associated devices, the number and position dependent upon the application: bar code reader/capper/decapper 1202; caps source 1232; pipette-tip rack space 1204; balance 1206; liquid vial deck space; particle-sized injection port 1208; viscometry injection port(s) 1210; drain waste station(s) 1212; gel dispensers 1220; orbital shaker 1214; heated block(s) 1216 and heated pipette tips 1218.

Bar code reader/capper/decapper 1202 is used for identifying and opening vessels that are capped and closing vials before they are sent to storage. In a preferred embodiment cap source 1232 provides a source for about 2000 caps. Balance 1206 is used for confirming the dispense by weight. Liquid vial deck space enables other sources of normal liquids to be placed on the deck. Similarly, in a preferred embodiment, enough space is provided to contain the racks and to re-order the vials into classes. Samples are pipetted into particle-sized injection port 1208. Viscometry injection port(s) 1210 allow for measurement of viscosity at different shear rates. Orbital shaker with heating and cooling capability 1214 is where mixtures requiring agitation, such as unstable suspensions, are delivered after decapping. Orbital shaker 1214 can also be used for mild mixing such as dissolution. With careful selection of the shaker, even more aggressive agitation can be achieved. Materials are placed upon/within heated block(s) 1216 for melting. The materials are then readied for dispensing. Heated pipette tips 1218 can be preloaded and heated for dispensing small quantities of meltables.

The off deck is mounted with devices, including but not limited to: second particle size detector 1222 and flush system; second viscometer electronics 1224; second valve and pump system 1226 for dispensing small (10's of micro liter) volumes of samples with a 'majority solvent' flush to the dispense needle; trash receptacle 1234; dilution port 1236;

second particle microscopy system 1238, and pump and source of common wash fluid connected to its needle 1228.

In this embodiment, the gel, paste and high viscosity fluid dispensing or the meltables dispensing (See FIG. 5) can require separate mixing station 1230. When mixing is not required, the dispense volume is confirmed using balance 1206. However, as order of addition and mixing do not allow the tip of any dispenser to contact the mixed formulation, the dispensing must be conducted without touch-off.

Process Description

The automated robotic system is designed to operate without manual interference for a minimum duration of, but not limited to, one day after it is initialized and loaded with relevant components (raw materials, consumables, vials and racks) in the set up phase. Each vial 104 in any given rack 102 represents a unique experiment and has its own set of parameters such as, but not limited to, number of components, type and quantity of each component, mixing time, comminution time, etc. The tool heads on solid dispensing station 400, liquids, suspensions, gels and meltables dispense station 500, normal liquids dispensing, and pipetting, and characterization station 600 and flexible arm station 800 are capable of handling both racks 102 and single vials 104. However, arm 302, used for transfer between stations in one embodiment, can handle only racks 102. Hence, the vials 104 are always grouped together in racks 102 when being transferred between stations. Once on a station, vials 104 can be picked up by the tool head and taken to the required locations for processing.

The actual working of the system is described in this section with the help of two examples: 1/experiment for preparing and testing Solution in Water (SL) emulsion formulation; and 2/experiment for preparing and testing Suspension Concentrate (SC) emulsion formulation.

In the first example, the initialization and set up phase have also been elaborated upon to illustrate the steps involved in preparing the system for a batch of experiments.

EXAMPLE 1

Experiment for Preparing and Testing Solution in Water (SL) Emulsion Formulation The objective of this experiment is to prepare a clear formulation, within a certain pH range, containing one active ingredient and three different additives. Successful formulations are then further tested for their chemical and/or biological activity. The steps involved in this experiment are as follows:
1) Add additives in the vial
2) Add active ingredients in the vial
3) Add water in the vial
4) Mix at low shear for 30 seconds
5) Heat the mixture for 10 minutes at 60° C.
6) Mix at high shear for 2 minutes
7) Conduct phase analysis
8) Store the clear samples for 24 hours and reject others
9) After 24 hours, conduct phase analysis on stored samples
10) Store the clear samples for further analysis and reject others In the current example, the component properties and quantities in one particular experiment are assumed to be as those described in the Table below.

| Component | Type | Quantity (mL or g) |
| --- | --- | --- |
| Additive 1 | Low viscosity liquid | 0.6 |
| Additive 2 | High viscosity liquid | 0.6 |
| Additive 3 | Solid | 0.6 |
| Active ingredient | Low viscosity liquid | 7.6 |
| Water | Low viscosity liquid | 1 |

Figure 13:
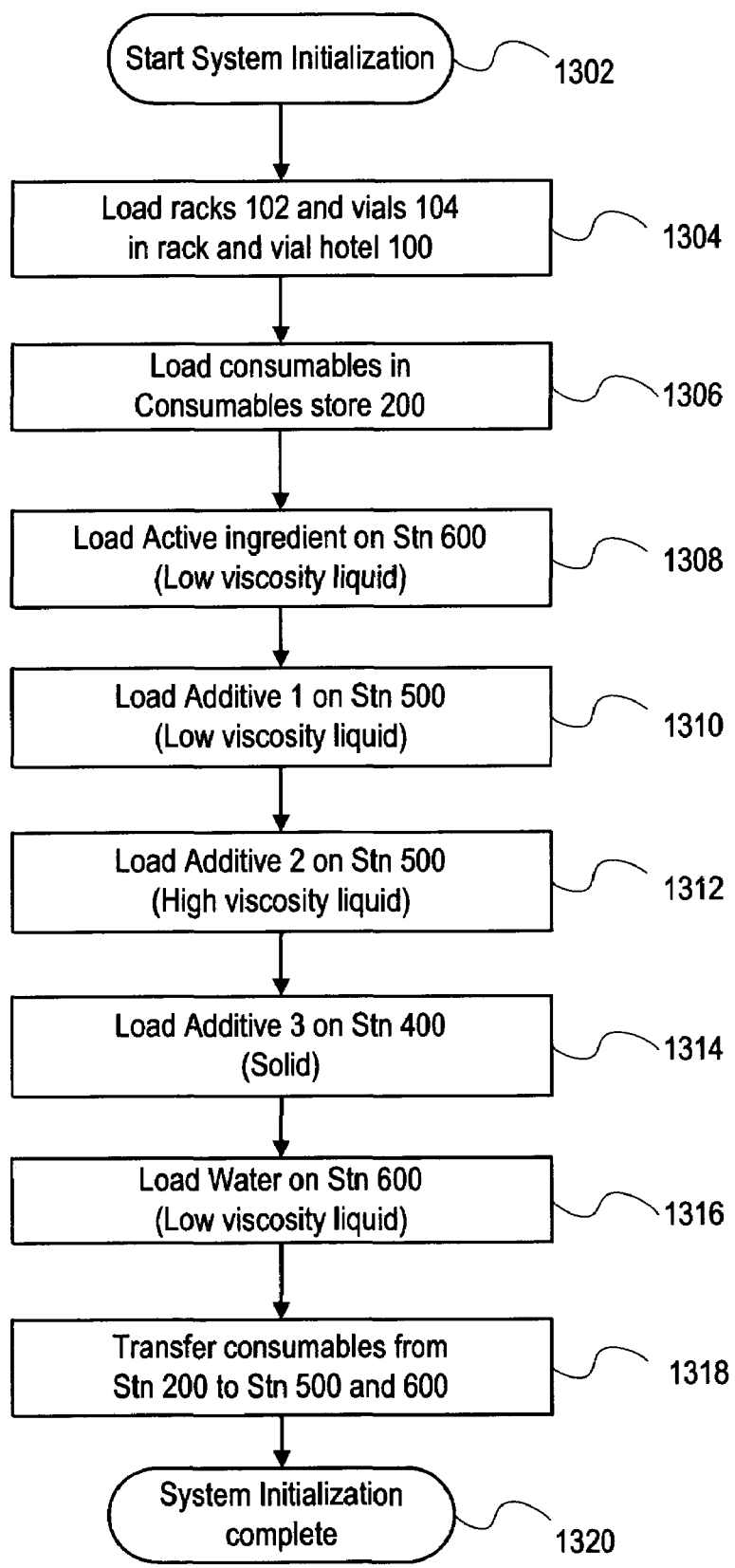
FIG. 13 illustrates an exemplary flow diagram for system set-up.

Before the experimentation can begin, the system undergoes a set-up phase comprising of the following steps:
1) Load racks and vials in the rack and vial storage system 100
2) Load consumables in consumables station 200
3) Load components on appropriate stations
4) Transfer consumables to appropriate stations The entire set-up procedure for the current experiment is represented in FIG. 13 in the form of a work-flow diagram and is further elaborated herein.

FIG. 13 illustrates the steps involved in the set-up phase of the system before experimentation can begin for preparing and testing Solution in Water (SL) emulsion formulation. The various steps involved in executing each block of the flow diagram are described below in detail, we note that this description is for illustration purposes only, various embodiments will necessitate various steps in various orders as will be readily seen by the experienced practitioner.

Start system initialization step 1302, is the first step of initialization. Here, the entire system is switched on and a primary system check is conducted by the operator.

The next step is loading racks and vials step 1304, where the required number of racks 102 and vials 104 are loaded in rack and vial storage system 100.

In loading consumables step 1306 all consumables such as but not limiting to pipette tips are loaded in consumables storage system 200.

In load active ingredient step 1308, active ingredient(s) are loaded on liquid dispensing, pipetting, characterization station 600. In a preferred embodiment, the active ingredients are loaded through the bottles connected to valve and pump system 626.

In load additive one, step 1310, additive one is loaded on liquids, suspensions, gels, and meltables dispensing station 500. In a preferred embodiment loading occurs at rack or dispensing locations 504.

In load additive two, step 1312, additive two being high viscosity liquid, can be dispensed by movable gel dispensers 502 on liquids, suspensions, gels and meltables dispense station 500 and hence are loaded in one of gel dispensers 502.

In load additive three, step 1314, additive three being a solid, is dispensed at solid dispensing station 400. It is loaded in one of solid source hoppers 404 and can be placed either directly on solid dispensing station 400 or in rack 102 in consumables storage system 200. From consumables storage system 200, rack 102 containing hopper 404, can then be picked up by robotic arm 302 and transported on rail 304 to solid dispensing station 400.

In load water step 1316, water is loaded on liquid dispensing, pipetting, characterization station 600 through a bottle(s) connected to valve and pump system 626.

In transfer consumables step 1318, consumables such as but not limited to pipette tips, are picked up from consumables storage system 200 by robotic arm 302 and transferred on rail 304 to liquids, suspensions, gels, meltables dispense station 500 and normal dispensing, pipetting, characterization station 600.

Finally, in system initialization complete step 1320, after all components are loaded and consumables transferred, the system is ready to start the experiments.

Figure 14:
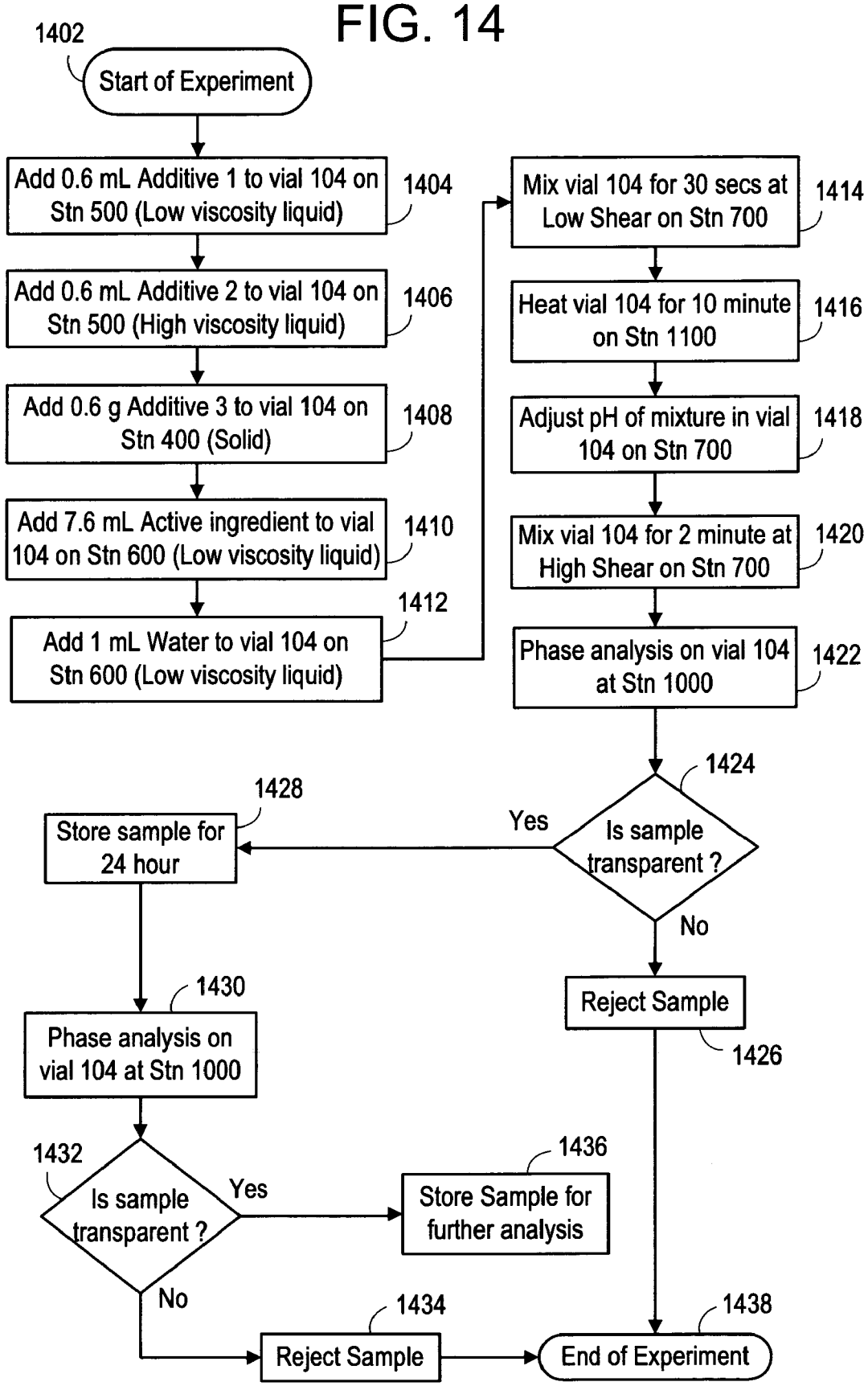
FIG. 14 illustrates flow diagram of experiment for preparing and testing Solution in Water (SL) formulation.

FIG. 14 illustrates the flow diagram of the experiment for preparing and testing Solution in Water (SL) formulation. The various steps involved in executing each block of the flow diagram are described below in detail. As before, we note that this description is for illustration purposes only, various embodiments will necessitate various steps in various orders as will be readily seen by the experienced practitioner.

At start of experiment step 1402, rack 102 containing as many as, but not limited to, six empty vials 104 is picked up by arm 302 and transferred to rack 102 entry point on liquids, suspensions, gels, meltables dispense station 500. From here, it is moved to rack or dispensing locations 504 by the tool head on liquids, suspensions, gels and meltables dispense station 500.

In add additive one, step 1404, the tool head picks up vial 104 from rack 102, takes it to barcode reader/decapper 508 for barcode scanning and puts it back in rack 102. Based on the barcode, the control software determines the component, in this case additive one, to be dispensed in vial 104. For the current experiment, the tool head picks up a disposable pipette from pipette-tip rack space 518, aspirates 0.6 mL of additive 1 and dispenses it in the appropriate vial 104 in rack 102. The tool head then moves above the trash collection chute 520 to dispose of the pipette tip.

In add additive two, step 1406, additive two being a high viscosity liquid, is dispensed gravimetrically. The tool head transfers vial 104 from its rack 102 to mass balance 516, which is then initialized and tare weight determined by the control software. The tool head then picks up movable gel dispenser 502 containing additive two, brings it over vial 104 and dispenses the additive two in discreet shots of 0.1 g until the balance registers 0.6 g. It then takes movable gel dispenser 502 back to its location and transfers vial 104 back in rack 102. When all the dispense tasks of the liquids, suspensions, gels, meltables dispense station 500 are completed, rack 102 with all its vials 104 is transferred to rack 102 exit point on liquids, suspensions, gels and meltables dispense station 500.

In add additive three, step 1408, rack 102 is picked up from rack 102 exit point on liquids, suspensions, gels and meltables dispense station 500 by arm 302 and transferred to the rack 102 entry point of solid dispensing station 400 for dispensing additive three. From there, vial 104 is first taken to barcode reader 406 for barcode scanning and then placed on mass balance 402 by the tool head on solid dispensing station 400. From the barcode, the control software confirms the solid to be dispensed, in this case additive three, which needs to be dispensed in vial 104. In the current example, hopper 404 containing additive three is picked up by the tool head and 0.6 g of additive three is added in vial 104 on mass balance 402. When all solid dispensing tasks are completed, rack 102 is transferred to rack 102 exit point on solid dispensing station 400.

In add active ingredient step 1410, arm 302 picks up rack 102 from the exit point on solid dispensing station 400 and transfers it to rack 102 entry point on normal liquids dispensing and pipetting, and characterization station 600. The tool head picks up rack 102 from entry point and transfers it to rack 102 buffer zone. There, 7.6 mL of active ingredient is added volumetrically in the vial 104 by the needle on tool head from the active ingredient reservoir connected to valve and pump system 626.

In add water step 1412, after adding active ingredient, the needle on tool head is rinsed in wash station 628 and then 1 mL of water is dispensed from the water reservoir connected to valve and pump system 626. Rack 102 is then moved to rack 102 exit point on normal liquids dispensing and pipetting, and characterization station 600.

In mix vial step 1414, arm 302 transfers rack 102 from exit point on normal liquids dispensing and pipetting, and characterization station 600 to rack 102 entry point 808 next to flexible arm 802. Flexible arm 802 moves rack 102 from there to the rack storage space for emptied rack 810. Vial 104 is picked up by flexible arm 802, taken to barcode reading station 804 for identification and then placed on mixer/homogenizer station 704 on mixer/homogenizer station 700. Parallel mixing stations 702 moves over up to six vials 104 placed on six parallel mixer/homogenizer stations 704, moves vertically down till mixers are in vials 104, and then starts mixing at low shear for 30 seconds. When the mixing time is complete, six parallel mixer/homogenizer stations 704 move vertically up till they are out of vials 104, move to the ultrasonic bath 706 to get washed and then move to the rinse station 708 to get rinsed. The vials are moved back from mixer/homogenizer stations 704 to rack 102 in the rack storage space for emptied rack 810. Rack 102 is then moved to rack 102 exit point.

In heat vial step 1416, arm 302 transfers rack 102 from rack 102 exit point on flexible arm station 800 to the temperature buffers 1100 where it is kept at 60° C. for 10 minutes.

In adjust pH step 1418, after 10 minutes, rack 102 is again transferred to rack 102 entry point 808 next to flexible arm 802. Flexible arm 802 moves rack 102 from there to the rack storage space for emptied rack 810. Vial 104 is picked up by flexible arm 802, taken to barcode reading station 804 for identification and then placed on mixer/homogenizer station 700 for pH adjustment. Mixer/homogenizer 704 shaft has on it a pH probe connected to pH multimeter 720, which measures the pH of mixture in vial 104 and controls the addition of acid/base via two valves 718 to reach the set-point value.

In mix vial step 1420, when the pH of mixture is within the desired range, the mixture in vial 104 is mixed at high shear for two minutes by the mixer/homogenizer 704. After mixing, the mixer/homogenizers 704 move vertically up till they are out of the vials 104, move to ultrasonic bath 706 to get washed and then moved to rinse station 708 to get rinsed. Vial 104 is moved back to rack 102 on the rack storage space for emptied rack 810 by flexible arm 802. The rack 102 is then moved to rack 102 exit point by the flexible arm 802.

In phase analysis step 1422, arm 302 transfers rack 102 from rack 102 exit point by flexible arm 802 to rack 102 entry point on phase stability and cloud point station 1000. Tool head 1004 on this station picks up the 104 from rack 102 with gripper 1006, takes it to barcode reader 1010 for identification and then puts it on turbidity analysis instrument 1008 for phase analysis.

In determination step 1424, the analysis results are analyzed by the software and the mixture is classified into categories such as, but not limited to, "Transparent", "Turbid", "Foamy", "Two-phase" etc.

If the mixture in vial 104 is not identified as "Transparent", in rejection step 1426, it is flagged as "rejected", and moved to rack 102, reserved for rejected samples, by tool head 1004. This rack 102, when filled, is moved to rack 102 exit point by tool head 1004, picked up by arm 302 and transferred back to the rack and vial storage system 100.

This brings the system to end point 1438, the experimental run is considered to be finished in the system.

However, if the mixture in vial 104 is identified as "Transparent" by the instrument 1008, in storage step 1428, it is flagged as "passed", and moved to rack 102, reserved for "passed" samples, by tool head 1004. This rack 102, when filled, is moved to rack 102 exit point by tool head 1004, picked up by arm 302 and transferred back to rack and vial storage system 100 in a space reserved for "passed" samples and stored for 24 hours. In phase analysis step 1430, after 24 hours, arm 302 picks up rack 102 containing "passed" samples again from rack and vial storage system 100 and transfers them to rack 102 entry point on phase stability and cloud point station 1000. Tool head 1004 on this station picks up vial 104 from rack 102 with gripper 1006, takes it to barcode reader 1010 for identification and then puts it on turbidity analysis instrument 1008 for phase analysis.

In second determination step 1432, the analysis results are again analyzed by the software and the mixture is classified into categories such as, but not limited to "Transparent", "Turbid", "Foamy", "Two-phase" etc.

As before, in second in rejection step 1434, if the mixture in vial 104 is not identified as "Transparent", then it is flagged as "rejected", and moved to rack 102, reserved for rejected samples, by tool head 1004. This rack 102, when filled, is moved to rack 102 exit point by tool head 1004, picked up by arm 302 and transferred back to the rack and vial storage system 100.

This brings the system to end point 1438, the experimental run is considered to be finished in the system.

However, if the mixture in vial 104 is identified as "Transparent" by the instrument 1008, in storage step 1428, it is flagged as "passed", and moved to rack 102, reserved for "passed" samples, by tool head 1004. This rack 102, when filled, is moved to rack 102 exit point by tool head 1004, picked up by arm 302 and transferred back to rack and vial storage system 100 in a space reserved for "passed" samples and stored for future analysis.

This brings the system to end point 1438, the experimental run is considered to be finished in the system

EXAMPLE TWO

Experiment for Preparing and Testing Suspension Concentrate (SC) Emulsion Formulations The objective of this experiment is to prepare a suspension concentrate emulsion formulation, within a certain particle size distribution and viscosity range, containing one active ingredient and two different additives. Successful formulations are then further tested for their chemical and/or biological activity. The steps involved in this experiment are as follows:

1) Add additives in the vial
2) Add active ingredients in the vial
3) Add water in the vial
4) Comminute mixture for 60 minutes
5) Measure particle size distribution
6) If sample is within the desired particle size range, then measure viscosity. Else, reject the sample.
7) If sample is within the desired viscosity range, then the sample is stored for further analysis. Else, the sample is rejected.

In this experiment, the component properties and quantities are assumed to be as those described in the Table below.

| Component | Type | Quantity (mL or g) |
|---|---|---|
| Additive 1 | Low viscosity liquid | 1.0 |
| Additive 2 | High viscosity liquid | 1.0 |

-continued

| Component | Type | Quantity (mL or g) |
|---|---|---|
| Active ingredient | Solid | 4.0 |
| Water | Low viscosity liquid | 4.0 |

Before starting the experiment, the automated robotic system undergoes the initialization and set-up phase, as was described in the earlier example.

Figure 15:
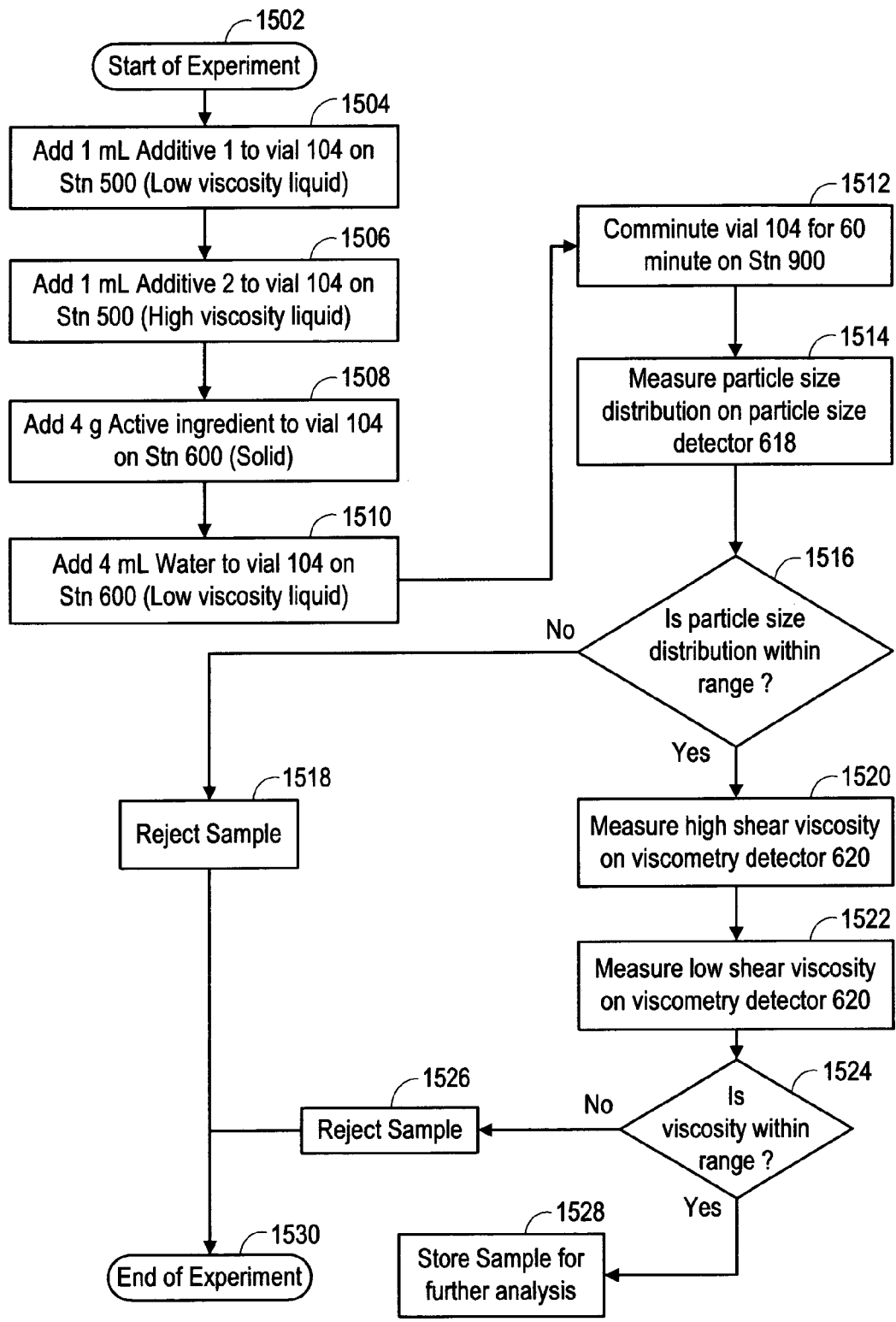
FIG. 15 illustrates flow diagram of experiment for preparing and testing Suspension Concentrate (SC) emulsion formulation.
Figure 16:
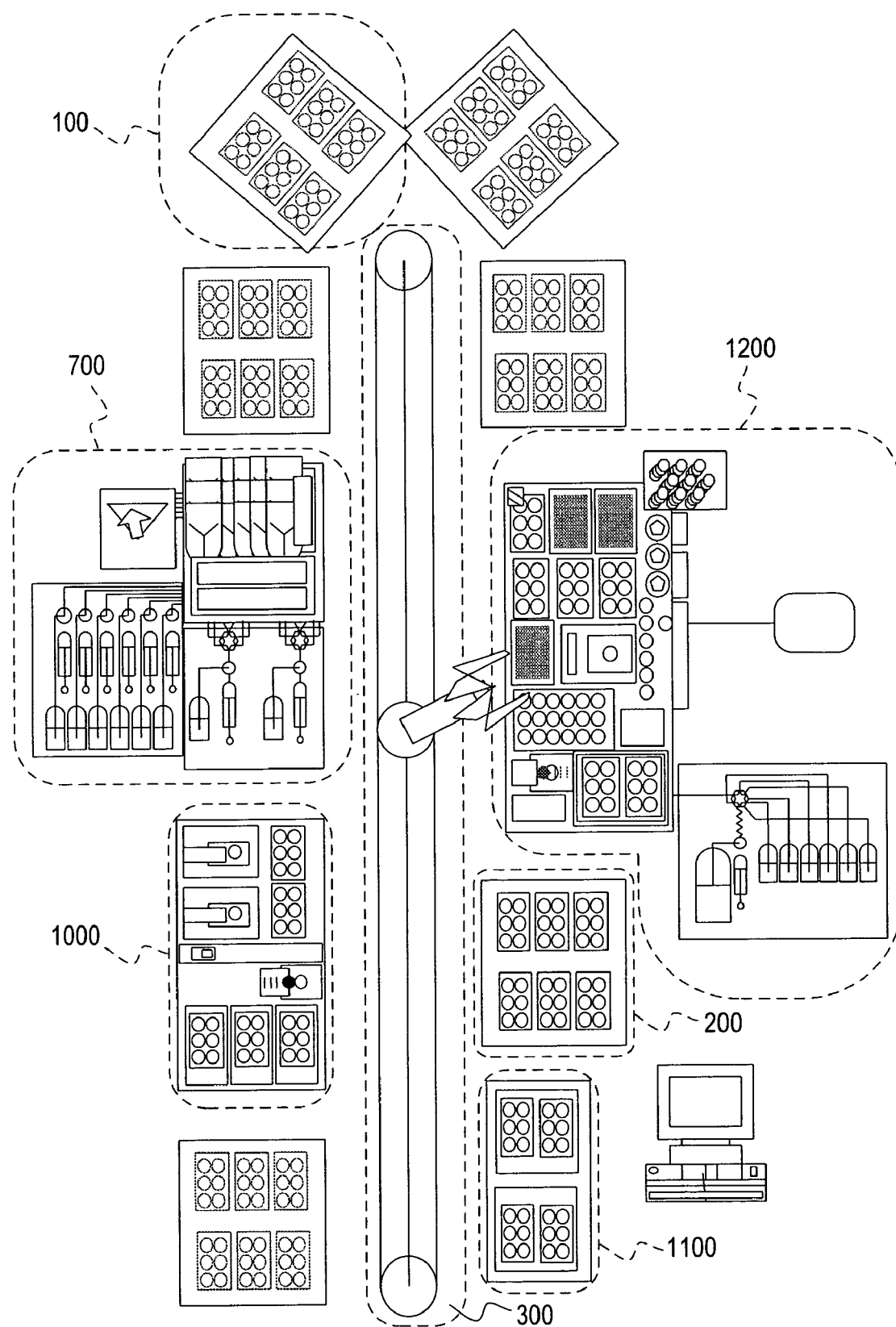
FIG. 16 illustrates an embodiment of the present invention comprising rack and vial storage system 100, consumables store 200, robotic arm 300, mixing or homogenizing station 700, phase stability and cloud point station 1000, buffers 1100, and dispensing, pipetting, and characterization station 1200.
Figure 17:
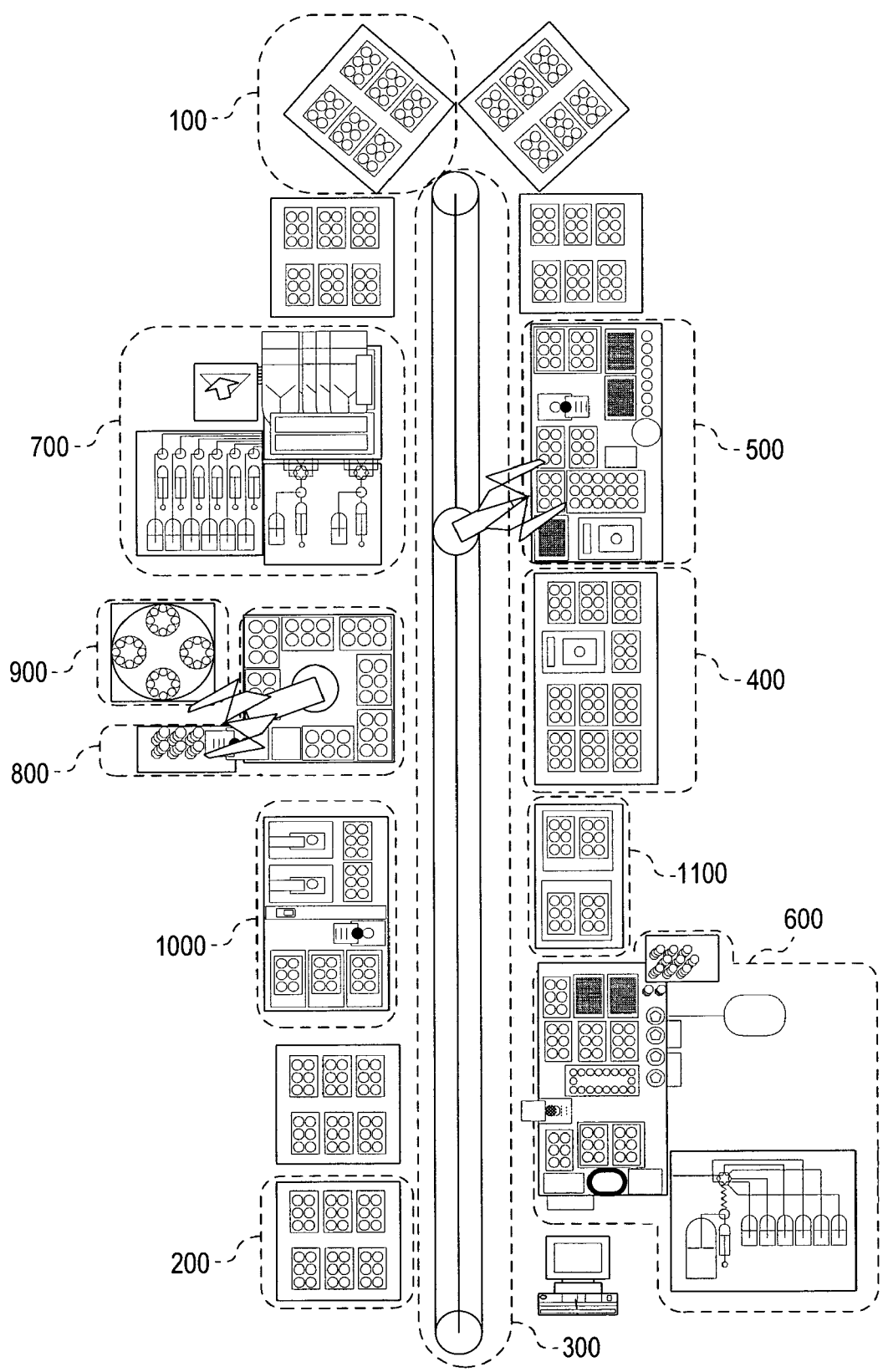
FIG. 17 illustrates an embodiment of the present invention comprising rack and vial storage system 100, consumables store 200, robotic arm 300, solid dispensing station 400, liquids, suspensions, gels and meltables dispense station 500, liquids dispensing and pipetting and characterization station 600, mixing or homogenizing stations 700, flexible arm station 800, comminutor station 900, phase stability and cloud point station 1000, and buffers 1100.

FIG. 15 illustrates the flow diagram of the experiment for preparing and testing Suspension Concentrate (SC) emulsion formulation. The various steps involved in executing each block of the flow diagram are described below in detail. We again we note that this description is for illustration purposes only, various embodiments will necessitate various steps in various orders as will be readily seen by the experienced practitioner.

At start of experiment step 1502, rack 102 containing as many as, but not limited to, six empty vials 104 is picked up by arm 302 and transferred to rack 102 entry point on liquids, suspensions, gels, meltables dispense station 500. From here, it is moved to rack or dispensing locations 504 by the tool head on liquids, suspensions, gels and meltables dispense station 500.

In add additive one, step 1504, the tool head picks up vial 104 from rack 102, takes it to barcode reader/decapper 508 for barcode scanning and puts it back in rack 102. Based on the barcode, the control software determines the component, in this case additive one, to be dispensed in vial 104. For the current experiment, the tool head picks up a disposable pipette from pipette-tip rack space 518, aspirates 1.0 mL of additive 1 and dispenses it in the appropriate vial 104 in rack 102. The tool head then moves above trash collection chute 520 to dispose of the pipette tip.

In add additive two, step 1506, additive two being a high viscosity liquid, is dispensed gravimetrically. The tool head transfers vial 104 from rack 102 to mass balance 516, which is then initialized and the tare weight determined by the control software. The tool head then picks up movable gel dispenser 502 containing additive two, brings it over vial 104 and dispenses the additive two in discreet shots of 0.1 g until the balance registers 1.0 g. It then takes movable gel dispenser 502 back to its location and transfers vial 104 back in rack 102. When all the dispense tasks of liquids, suspensions, gels, meltables dispense station 500 are completed, rack 102 with all vials 104 is transferred to rack 102 exit point on liquids, suspensions, gels and meltables dispense station 500.

In add active ingredient step 1508, rack 102 is picked up from rack 102 exit point on liquids, suspensions, gels and meltables dispense station 500 by arm 302 and transferred to rack 102 entry point of solid dispensing station 400 for dispensing active ingredient. From there, vial 104 is first taken to barcode reader 406 for barcode scanning and then placed on mass balance 402 by tool head on solid dispensing station 400. From the barcode, the control software determines the solid, in this case active ingredient, which is to be dispensed in vial 104. In the current example, hopper 404 containing active ingredient is picked up by the tool head and 4.0 g of active ingredient is added in appropriate vial 104. When all solid dispensing tasks are completed, rack 102 is transferred to rack 102 exit point on solid dispensing station 400.

In add water step 1510, arm 302 picks up rack 102 from exit point on solid dispensing station 400 and transfers it to rack 102 entry point on normal liquids dispensing and pipetting, and characterization station 600. The tool head picks up the rack from entry point and transfers it to rack 102 buffer zone. Here, 4.0 mL of water is added volumetrically in vial 104 by the needle on tool head from the active ingredient reservoir connected to the valve and pump system 626. After adding water, the needle on tool head is rinsed in wash station 628 and rack 102 is then moved to rack 102 exit point on normal liquids dispensing and pipetting, and characterization station 600.

In comminution step 1512, beads are first added in vial 104 using a solids canula on the liquids, suspensions, gels, meltables dispense station 500. Arm 302 transfers rack 102 from exit point on normal liquids dispensing and pipetting, and characterization station 600 to rack 102 entry point on liquids, suspensions, gels and meltables dispense station 500, from where it is moved to the rack or dispensing locations 504. The canula on the tool head of liquids, suspensions, gels and meltables dispense station 500 aspirates the required quantity of beads from the comminuting bead source 506 and dispenses them volumetrically into vial 104. The rack is then moved to rack 102 exit point on liquids, suspensions, gels and meltables dispense station 500 by the tool head and transferred by arm 302 to rack 102 entry point 808 next to flexible arm 802. Flexible arm 802 then moves rack 102 to the rack storage space for empty racks 810. Vial 104 is picked up by flexible arm 802, taken to capping/decapping/barcode reading/cap supply station 804 for identification and capping. In the capping/decapping/barcode reading/cap supply station 804, when capping vial 104 in one embodiment, a cap is dispensed from the cap supply and held on the mouth of vial 104 by the tool head. Vial 104 is capped by rotating it around its central vertical axis and then placed in one of comminution locations 904 at defined stop position 908 on vial holder 906 of comminution station 900 by flexible arm 802. The lid on comminution station 900 is closed and vial holders 906 are then rotated in planetary motion for 60 minutes. At the end of the comminution time, vial holder 906 stops at defined stop position 908, and vial 104, is picked up by flexible arm 802 and transferred back to rack 102 in the rack storage space for emptied rack 810. Rack 102, when filled, is moved by flexible arm 802 to rack 102 exit point 808, from where it is transferred by arm 302 to rack 102 entry point on normal liquids dispensing, pipetting, characterization station 600 for bead removal. Vial 104 is moved to barcode reader/capper/decapper 602 by tool head on normal liquids dispensing and pipetting, and characterization station 600. In one embodiment, the cap on vial 104 is gripped by the barcode reader/capper/decapper 602 tool head and vial 104 is rotated to be decapped. The cap is disposed of in trash 632 and vial 104 is moved to back to rack 102. Using special pipettes from the pipette-tip rack space 604, only the suspension in vial 102 is aspirated and dispensed into new vial 104 in a different rack 102 in the rack buffer space. The barcode of new vial 104 containing the suspension is read at the barcode reader/capper/decapper 602. The original vial 104 and rack 102 can then be sent to the rack and vial storage system 100 using arm 302 or remain on the station for characterization.

In particle size distribution measuring step 1514, for measuring the particle size distribution, the tool head picks up a pipette from pipette-tip rack space 604, aspirates between 0.5 and 1.0 mL of suspension from vial 104 and injects it in the particle-size detector injection port 610. This port allows dilution of the sample before measuring.

In determination step 1516, the injected sample is analyzed in the off-deck mounted particle analyzer 618 and the particle size distribution profile is generated. This profile is then compared by the software with the desired profile and based on the comparison; the samples are classified as "failed" or "passed".

In rejection step 1518, if the measured particle size distribution of the sample from vial 104 is out of the desired range, then the formulation in that vial 104 is classified as "failed" and is not tested further. It can be transferred in another rack 102, reserved for "failed" formulation and transferred to rack and vial storage system 100 when it is filled with vials 104.

This brings the system to end point 1530, the experimental run is considered to be finished in the system.

If the measured particle size distribution of the sample from vial 104 is within the desired range, then the formulation in that vial 104 is classified as "passed" and its viscosity is measured at both high-shear and low-shear. In high shear viscosity measurement step 1520 and in low sheer viscosity measurement step 1522 the tool head picks up a pipette from pipette-tip rack space 604, aspirates between 0.5 and 1.0 mL of suspension from vial 104 and injects it in the viscometry injection port(s) 612. The high shear and low shear measurements are conducted in two different viscometer detectors 620. After the measurement is complete, viscometry injection port(s) 612 and off deck viscometer detectors 620 are automatically washed and cleaned.

In viscosity determination step 1524, the measured viscosities are compared with the desired values. If the measurements are within the desired range, then the samples are classified as "passed". If not, they are classified as "failed".

In viscosity rejection step 1526, samples classified as "failed" are not tested further and can be transferred to another rack 102, reserved for "failed" formulations. This rack is moved to vial storage system 100 when filled with vials 104.

This brings the system to end point 1530, the experimental run is considered to be finished in the system.

If the formulation in vial 104 is classified as "passed", then in storage step 1528 the formulation is moved by the tool head to rack 102, reserved for "passed" samples. This rack 102, when filled, is moved to rack 102 exit point by the tool head, picked up by arm 302 and transferred back to rack and vial storage system 100 in a space reserved for "passed" samples and stored for further analysis.

This brings the system to end point 1530, the experimental run is considered to be finished in the system.

Although the apparatus and process of the present invention has been described in detail for purpose of illustration, it is understood that such detail is solely for that purpose, and variations can be made therein by those skilled in the art without departing from the scope of the invention. The apparatus and operation of the present invention is defined by the following claims.

What is claimed is:

1. A modular robotic system comprising:
 a rack and vial storage system storing therein a plurality of racks and vials;
 a consumables storage system storing materials;
 a first, second and third location;
 a first robotic arm for transferring said vials from said first location to said second location, or for transferring said racks from said first location to said second location;
 a dispensing, pipetting or characterization station or solid dispensing station for dispensing active ingredients, water, or additives to said vials to yield a formulation, wherein said first robotic arm transfers materials from said consumables storage system to said dispensing, pipetting, or characterization station or to said solid dispensing station; a mixing or homogenizing station for mixing or homogenizing said, formulation to yield a mixture;
a phase stability station for phase analysis of said mixture;
optionally a liquids, suspensions, gels or meltables station and
optionally a capping, decapping, bar-code reading or cap-supply station;
wherein said first location is
said rack and vial storage system,
said dispensing, pipetting or characterization station,
said mixing or homogenizing station, or
said phase stability station; and
wherein said second location
said rack and vial storage system,
said dispensing, pipetting or characterization station,
said mixing, or
said phase stability station; and
a flexible second robotic arm, wherein said flexible second robotic arm transfers said racks or said vials from said first robotic arm to said third location upon said modular robotic system where said third location is said capping or decapping or bar-code reading or cap-supply station;
said rack and vial storage system,
said dispensing, pipetting or characterization station,
said mixing or homogenizing station,
said phase stability station,
said solid dispensing station or
said liquids, suspensions, gels or meltables station.

2. The modular robotic system of claim 1, further comprising a comminution station for grinding solid particles, wherein said solid particles are active ingredients or additives and wherein said flexible second robotic arm transfers said racks from said first robotic arm to said comminution station.

3. The modular robotic system of claim 1, wherein said racks each hold up to six said vials, wherein said racks are each bar coded and wherein said vials are each bar coded;
wherein said materials are selected from the group consisting of said vials, pipette tips, said active ingredients and said additives; and
wherein said dispensing, pipetting, or characterization station further comprises:
a waste station, wherein fluid may be pumped to waste; and
a tool head, wherein said tool head is fitted with at least one item selected from the group of items consisting of rack gripper, plate gripper, vial gripper, filter gripper, cap gripper, pipettor and dispense needle.

4. A modular robotic system comprising:
a rack and vial storage system storing therein a plurality of racks and vials;
a consumables storage system storing materials;
a first, second, and third location;
a first robotic arm for transferring said vials from said first location to a said second, or for transferring said racks from said first location to said second location;
a dispensing, pipetting or characterization station for dispensing active ingredients, water or additives to said vials;
a solid dispensing station for dispensing solids by weight into said vials, wherein said solids are active ingredients or additives;
a liquids, suspensions, gels or meltables station for dispensing viscous fluid, gels, pastes or meltables, wherein said high viscous fluids, said gels, paste and meltables are active ingredients or additives;
wherein said combination of said active ingredients, water, and additives from said dispensing, pipetting or characterization station, said solid dispensing station or said liquids, suspensions, gels or meltables station yields a formulation;
a mixing or homogenizing station for mixing or homogenizing said formulation to yield a mixture; and
a phase stability station for phase analysis of said mixture;
a flexible robotic arm station, including a flexible second robotic arm that transfers said racks from said first robotic arm to said third location upon said modular robotic system; and
a comminution station for grinding solid particles;
wherein said first location is;
said rack and vial storage system;
said dispensing, pipetting or characterization station
said mixing or homogenizing station;
said phase stability station;
said solid dispensing station;
said liquids, suspensions, gels; or meltables station; or
said comminution station;
wherein said second location is:
said rack and vial storage system;
said dispensing, pipetting or characterization station;
said mixing or homogenizing station;
said phase stability station:
said solid dispensing station;
said liquids, suspensions, gels, or meltables station:
said flexible arm station; or
said comminution station; and
wherein said third location is:
said rack and vial storage system;
said dispensing, pipetting or characterization station;
said mixing station:
said phase stability station;
said solid dispensing station;
said liquids, suspensions, gels or meltables station; or
said comminution station.

5. The modular robotic system of claim 4,
wherein said racks each holds up to six said vials, wherein said racks are each bar coded and,
wherein said vials are each bar coded;
wherein said materials are selected from the group consisting of said vials, pipette tips, said active ingredients and said additives; and
wherein said dispensing, pipetting or characterization station further comprises:
a waste station, wherein fluid may be pumped to waste;
a tool head, wherein said tool head is fitted with at least one item selected from the group of items consisting of: rack gripper, plate gripper, vial gripper, filter gripper, cap gripper, pipettor and dispense needle; and
a deck; wherein said deck is mounted with at least one device selected from the group of devices consisting of: bar code reader, decapper, cap source, orbital shaker, tank mix testing unit, injection port, dilution port, filtration device, particle size detector, viscometer, waste station, bead collector, photography system, trash collection chute and particle microscopy system.

6. The modular robotic system of claim 4,
wherein each said rack includes an identifying bar code; that is read by said first robotic arm.

7. The modular robotic system of claim 5,
wherein said liquids, suspensions, gels or meltables station further comprises:
a second tool head, wherein said second tool head is fitted with at least one item selected from the group of items consisting of rack gripper, plate gripper, vial gripper, gel dispensor gripper, cap gripper, pipettor and vacuum canula; and a second deck; wherein said second deck is mounted with at least one device selected from the group of devices consisting of: movable gel dispensor, comminuting bead source, bar code reader, decapper, orbital shaker, heated block, mass balance and trash collection chute.

8. The modular robotic system of claim 7, further comprising:

a second dispensing, pipetting or characterization station, wherein said second dispensing, pipetting or characterization station further comprises a third deck and a third tool head, wherein said third tool head is fitted with at least one item selected from the group of items consisting of rack gripper, plate gripper, vial gripper, gel dispensor gripper, cap gripper, pipettor and dispense needle; and wherein said third deck is mounted with at least one device selected from the group of devices consisting of: bar code reader, capper, decapper, caps source, balance, injection port, drain waste station, gel dispenser, orbital shaker and heated block.

9. The modular robotic system of claim 8, further comprising:

an off deck, wherein said off deck is mounted with at least one device selected from the list of devices consisting of second particle size detector, flush system, second viscometer and second particle microscopy system.

* * * * *